United States Patent [19]

Zaffaroni

[11] 4,186,184

[45] Jan. 29, 1980

[54] SELECTIVE ADMINISTRATION OF DRUG WITH OCULAR THERAPEUTIC SYSTEM

[75] Inventor: Alejandro Zaffaroni, Atherton, Calif.

[73] Assignee: Alza Corporation, Palo Alto, Calif.

[21] Appl. No.: 32,498

[22] Filed: Apr. 23, 1979

Related U.S. Application Data

[63] Continuation of Ser. No. 864,432, Dec. 27, 1977.

[51] Int. Cl.$^2$ .................. A61K 9/22; A61M 31/00
[52] U.S. Cl. .................... 424/14; 128/260; 424/16; 424/19; 424/21; 424/22; 424/28
[58] Field of Search ............... 128/260; 424/14–22, 424/28

[56] References Cited

PUBLICATIONS

J. Shell & R. Baker, Diffusional Systems for Controlled Release of Drugs to the Eye, Ann. Ophthalmol. 6:1037 (1974).
J. Shell, Ocular Therapy by Controlled Drug Delivery: the Ocusert System, Ophthalmic Surg, 5:73 (1974).
H. Armaly and K. Rao, The Effect of Pilocarpine Ocusert with Different Release Rates on Ocular Pressure, Invest. Ophthalmol. 12, 491 (1973).
V. A. Place, M. Fisher, S. Herbst, L. Gordon & R. C. Merrill, Comparative Pharmacologic Effects of Pilocarpine Administered to Normal Subjects by Eyedrops or by Ocular Therapeutic Systems, Amer. J. Ophthalmol. 80, 706 (1975), (above cited as footnotes #23–#26, p. 592).
S. K. Chandrasekaran, Harriet Benson & John Urquhart, Alza Corp., Palo Alto, Calif., Chapter 7, "Methods to Achieve Controlled Drug Delivery–The Biomedical Engineering Approach", pp. 557–572, 590–591. Robinson, J. R. Ed., "Sustained & Controlled Release Drug Delivery Systems, Marcel Dekker, Inc. N.Y., N.Y. (1978).

*Primary Examiner*—Shep K. Rose
*Attorney, Agent, or Firm*—Paul L. Sabatine; Thomas E. Ciotti; Edward L. Mandell

[57] ABSTRACT

A method for administering a drug to a preselected tissue compartment of the eye for advantageously controlling the concentration of drug in the tissue compartment is disclosed. The method comprises (1) placing an ocular therapeutic system in the eye, and (2) orienting the drug releasing portal of the system towards the preselected tissue compartment for controlled administration of drug thereto.

27 Claims, 10 Drawing Figures

STEADY STATE AQUEOUS HUMOR PILOCARPINE CONCENTRATION DURING DRUG DELIVERY FROM SINGLE PORTAL SYSTEMS: CONTRIBUTION OF DRUG RELEASED TOWARD BULBAR VS. PALPEBRAL CONJUNCTIVA

STEADY STATE ACQUEOUS HUMOR PILOCARPINE CONCENTRATION DURING DRUG DELIVERY ONLY TOWARD THE BULBAR CONJUNCTIVA OR TOWARD BOTH PALPEBRAL AND BULBAR CONJUNCTIVA

EFFECT OF RATE OF RELEASE ON STEADY STATE AQUEOUS HUMOR PILOCARPINE CONCENTRATION AT A CONSTANT SURFACE AREA

EFFECT OF THE RATE OF RELEASE AND SURFACE AREA ON STEADY STATE AQUEOUS HUMOR PILOCARPINE CONCENTRATION

SELECTIVE ADMINISTRATION OF DRUG WITH OCULAR THERAPEUTIC SYSTEM

This is a continuation, of application Ser. No. 864,432, filed Dec. 27, 1977.

FIELD OF THE INVENTION

This invention pertains to a method for delivering drug to preselected tissue compartments of the eye and for controlling the concentration of drug in the tissue compartments. The method effectively uses an ocular therapeutic system comprising drug, a delivery module, a platform and a drug program which operate as an integrated unit for delivering a therapeutically effective amount of drug at a controlled rate and pattern to preselected tissue compartments.

BACKGROUND OF THE INVENTION

A need existed, heretofore, for a method of administering drug to a preselected tissue compartment of the eye. More particularly, the need existed for a method that both administers drug to a preselected tissue compartment and controls the delivery of drug to achieve a well-defined concentration in the tissue compartment. This particular need existed because of the shortcomings associated with some of the prior art methods for administering drugs, mainly drops and ointments. For example, these methods are unsatisfactory because drops and ointments both result in the eye receiving drug that is administered indiscriminately to all tissue compartments including tissue compartments that do not need medication, and because these methods do not permit that the drug administered be kept at a well-defined concentration in the tissue compartments of the eye. Also, drops and ointments are wasteful, as they use excessive amounts of drug for treating a condition that can be treated with less drug, and because the drug is washed away by tears leaving the eye without drug until the next application of drug. Often, the tissue compartments receiving medication they do not need may exhibit unwanted side effects to the drug. See U.S. Pat. Nos. 3,149,035; 3,214,338; 3,415,929; 3,856,919; 3,872,865; 4,003,991; and Journal of Pharmaceutical Sciences, Volume 63, Number 3, pages 335 to 338, 1974.

Another prior art method for administering drug to the eye consisted in applying a lamella to the inner surface of the eyelid. Usually, lamella were made by dispersing drug in a water-soluble gel of glycerinated gelatin that dissolved rapidly in tear fluid producing the same effects obtained with drops and ointments. These effects include administering drug to all tissues of the eye, even to tissues that do not need medication. That is, lamella lack the ability to administer drug to preselected tissues compartments, and they do not possess any properties for evidencing any relation between the amount of drug administered and the concentration of drug in the tissue compartments of the eye. See Great Britain 1451, and in United States Patent No. 273,410; Pharmaceutical Sciences, by Remington, Volume XII, pages 547 to 548, 1965, published by Mack Publishing Company, Easton, PA, and An Introduction to Pharmaceutical Formulation, by Fishburn, Chapter 6, page 116, 1965, published by Pergamon Press Ltd. New York.

Ocular therapeutic systems for administering drug to the eye are known to ocular pharmacology and ophthalmic therapy in U.S. Pat. Nos. 3,416,530; 3,618,304; and 3,828,777, in United States Patent Application Ser. No. 569,953 filed on Apr. 21, 1975 and in United States Patent Application Ser. No. 578,979 filed on May 19, 1975. These patents and the patent applications are assigned to the ALZA Corporation of Palo Alto, Calif., the assignee of this patent application. The ocular systems disclosed in the patents and applications provide a complete ophthalmic course of therapy by administering drug for a prolonged period of time to the eye to produce a beneficial effect. These systems are made with a drug reservoir, a rate controller and a portal for releasing drug in a controlled therapeutic pattern to the eye and its surrounding tissues.

While the above ocular therapeutic systems are truly outstanding and represent a pioneering advancement in ocular drug delivery, and while they are useful for administering drug to the total environment of the eye, there are instances where the use of these systems can be inventively improved for more desirable therapy. For example, this invention makes possible the obtainment of the therapeutic benefit of a chosen drug and to control its concentration in a preselected tissue compartment by a preplanned cooperation, between the therapeutic system and the tissue compartment, effected through specific, directional controlled drug delivery in correlation with its concentration in a tissue compartment of the eye. The prior art lack of directional control coupled with a correlation in drug delivery makes it difficult to obtain the full therapeutic effect of a chosen drug and to regulate its concentration in the tissue compartment; particularly, if the drug is released to a tissue compartment distant and remote from the tissue compartment that really needs specific medication. The prior art methods of non-specific drug administration are wasteful, as they administer excessive drug that is lost through the nasolacrimal duct, by a rapid runoff of a swollen tear film, and because they administer drug to tissue compartments that do not need it. With these non-specific methods of administration, only a fraction of drug remains available for penetration into a preselected tissue compartment, or for introduction at a specific loci of the eye for entrance into systemic circulation.

OBJECTS OF THE INVENTION

Accordingly, it is an immediate object of this invention to provide a method for administering drug using an ocular therapeutic system which method overcomes the shortcomings and limitations associated with the prior art by selectively administering drug to a preselected tissue compartment of the eye.

Another object of the invention is to provide a method for selectively administering drug to a particular tissue compartment of the eye which method increases the bioavailability of ophthalmic drug administered to certain anatomical tissues of the eye by administering drug from an ocular therapeutic system having a single drug emitting portal that emits drug preferentially to that tissue and concomitantly eliminates drug waste, avoids administering drug where it is not needed, and substantially lessens the likelihood of side effects.

Another object of the invention is to provide a method for administering predominately to the eye surface locally acting drug, for administering internally to the eye internally acting drug, or for administering to a systemic drug receiving portal of entry systemic drug, which drug produces a physiological or pharmacological effect when administered by systems having selective capacity to deliver drug to the preselected drug tissue compartment.

Another object of the invention is to provide a method for controlling the drug delivery rate to and drug concentration in selected tissues of the eye by orienting the portal, controlling the area of the drug releasing portal and the rate of drug released from an ocular therapeutic system exposed to the selected drug receiving tissue of the eye.

Still yet another object of the invention is to provide a method for delivering drug which method uses an ocular therapeutic system having a drug emitting portal that directionally releases drug into the adjacent thin tear film positioned between the emitting portal and a contacting membrane of the eye for penetration into the eye membrane with minimal lateral dispersion of drug, and which method and system can be placed in the eye for administering drug to the bulbar conjunctiva or the palpebral conjunctiva.

Still a further object of this invention is to provide a method of delivering drug for medical and veterinary application which method uses an ocular therapeutic system having increased specificity of drug delivery obtained by manufacturing the system with a fixed oriented drug delivery portal, and which system when positioned in the eye directs drug to the eyeball for delivery to the inside of the eye, or away from the eyeball for delivery to eye tissues within the eye cavity.

Yet a further object of the invention is to provide a method of using an ocular therapeutic system that has a sole unidirectional drug emitting surface for delivering drug preferentially to a single drug receiving tissue compartment of the eye, and which method and one-sided releasing system achieve double clinical duration of drug delivery by delivering the same amount of drug present in a two-sided emitting system from the single emitting surface of the one-sided system.

Other objects, features and advantages of the invention will be more apparent to those skilled in the art from the following detailed description taken in conjunction with the drawings and the accompanying claims.

SUMMARY OF THE INVENTION

This invention concerns a method for selectively administering drug to a preselected tissue compartment of the eye and for controlling the amount of drug in the tissue compartment. The method comprises (1) placing in the eye an ocular therapeutic system comprising: (a) a drug, (b) a drug delivery module comprising a reservoir for housing drug for execution of a therapeutic program, a rate controller which maintains drug delivery at the effective rate throughout the life of the system, an energy source for transferring drug from the reservoir to the tissue, and a portal for releasing drug from the module, and (c) a platform which integrates the module into a unit for placement and retention in the eye, and (2) orienting the portal towards a preselected tissue compartment for releasing drug thereto. The method uses a system that possess a delivery portal that can be given a fixed orientation in the eye, and which portal provides the exit path for drug emerging from a drug reservoir through the rate controller and for its selective delivery to the chosen tissue compartment. The orientation of the portal acting in cooperation and unity with the system that controls the rate of release of drug from the portal to the tissue, controls the concentration of drug from the portal to the tissue, and thereby controls the concentration of drug in the tissue compartment of the eye.

BRIEF DESCRIPTION OF DRAWINGS

In the drawings, which are not drawn to scale, but are set forth to illustrate various embodiments of the invention, the figures are as follows.

In the drawings and specification, like parts in related figures are identified by like numbers. The terms appearing earlier in the specification and in the description of the drawings, as well as embodiments thereof, are further described elsewhere in the disclosure.

DEFINITION OF TERMS AND DETAILED DESCRIPTION OF THE INVENTION

The expression therapeutic system as used herein denotes a controlled dosage form which provides a pre-programmed, unattended delivery of drug at a rate, and for a time period, established to meet a specific therapeutic need. A therapeutic system comprises four components, (1) a drug, (2) a drug delivery module, (3) a platform and (4) a drug program. The drug released by the system is a locally or systemically acting drug that produces a physiological or pharmacological beneficial effect. The drug delivery module comprises four members; (a) a drug reservoir for housing drug in an amount needed for carrying out a prescribed therapeutic program, (b) a rate controller which establishes and maintains the rate of drug administered, (c) an energy source that effects the transfer of drug from the reservoir to the selected point of release in the eye, and (d) a delivery portal which provides an exit for the drug from the drug delivery module and specifically directs the drug to a preselected site. The platform unites and integrates the components of the system into a unit manufactured device adapted for the biological environment. Finally, the drug program administers the drug in the most beneficial manner to produce the desired therapeutic effect. These components of the therapeutic system are described immediately below.

The expression "tissue compartments of the eye" as used herein denotes the anatomical tissues and structures of the eye including (a) the eyeball, (b) tissues and structures proximal to the eyeball and (c) tissues and structures distant to the eyeball. The eyeball includes the external or outside tissues such as the sclera, cornea and bulbar conjunctiva. The eyeball includes internal or inside tissues and structures such as the aqueous humor, vitreous humor, lens, iris, ciliary body, ciliary muscle, canal of Schlemm, choroid and retina. The tissues proximal to the eyeball include the palpebral conjunctiva, tear film, the lids and their associated secretory glands, and the edge of the eye. The tissues distant to the eyeball include the nose and throat and their mucosal surfaces, and other body tissues that can be reached through the nose and throat. The anatomy of the eye is disclosed in *General Ophthalmology*, 7th Edition, 1974, by Vaughan and Asbury, published by Lange Medical Publications, Los Altos, Calif., and in *The Eye*, Volume 1, 1969, by Davson, published by Academic Press, New York.

Figure 1:
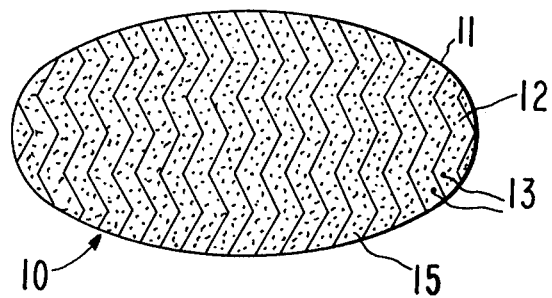
FIG. 1 is a cross-sectional view of an ocular therapeutic system formed with a unidirectional drug releasing portal for releasing drug housed therein.

Turning now to the drawings in detail, which are examples of ocular therapeutic systems useful for releasing drug according to the selected method of administration of the invention to a particular tissue compartment or structure, and which examples are not to be construed as limiting, one embodiment of an ocular therapeutic system manufactured in the form of an ocular drug delivery device 10 is indicated in FIG. 1 by numeral 10. System 10, as seen in FIG. 1 in cross-section, is an ocular therapeutic system manufactured for administering a drug 13 to a particular drug tissue site of the eye. System 10 is a unidirectional drug releasing ocular therapeutic system. System 10 comprises a drug delivery module 11 made of a polymeric matrix, preferably a solid polymer, which matrix forms reservoir 15 for housing drug 13. Module 11 is formed with a controller 12 for controlling and governing the rate of release of drug 13 from system 10. In the embodiment described, rate controller 12 is a surface of the polymeric material which forms the last wall confining reservoir 15, and which material is permeable to the passage of drug 13 by diffusion. In operation, drug 13 is released from reservoir 15 by rate controller 12 which controller is a portal 12 for effecting exit of drug 13 from system 10 for transfer to a tissue compartment of the eye. The energy source for driving drug 13 from system 10 is the concentration gradient of drug 13 across the rate controller 12. The surfaces comprising the remainder of system 10, not shown in FIG. 1, are in a presently preferred embodiment non-emitting surfaces. These latter surfaces are made of a material impermeable to the passage of drug 13, or the remaining wall surfaces of reservoir 15 not seen in FIG. 1, are coated with a material impermeable to the passage of drug 13.

The method of the invention provides a new and useful means for controlling the concentration of drug 13 in a tissue compartment of the eye. The concentration is controlled by orienting portal 12 while simultaneously controlling the rate of release of drug 13 from system 10 and the surface area of portal 12. For example, by varying the surface area of portal 12 to preselected dimensions while holding the rate of release of drug 13 constant from system 10, a linear correlation is substantially established between the tissue concentration and the surface area of portal 12. Also, by varying the rate of release of drug 13 to a preselected amount of drug per period of time while maintaining the surface area of portal 12 constant, a linear correlation is established between the concentration of drug 13 in the tissue and the rate of release. The benefits provided by the invention from coordinating and knowing the orientation, surface area of the portal and the rate of release of drug thusly comprise (a) controlling the concentration of drug in the tissue accompanied by administering only needed amounts of drug for improved therapy, (b) letting the physician substantially know the concentration of drug in the tissue, and (c) providing a method for scientifically predicting the concentration of drug in the tissue. Additional benefits include (d) prolonging the useful life of the system by releasing drug housed in the reservoir from a single portal, (e) more economical therapy because the number of systems required is reduced for a given therapeutic program, and (f) drug waste is reduced by direct drug to target application. The additional benefits are achieved by the invention's contribution to ocular therapy. That is, there is a limited thickness for an ocular platform, encompassing the drug delivery module, that can be accepted by an animal's eye, which includes the human eye. This limits drug reservoir capacity, resulting in limited duration. Duration is of fundamental value for patient compliance and cost of the system. A two-sided system waste approximately one-half the drug, while a one-sided system has a duration twice as long with patient compliance and reduced cost benefit to the patient.

In another embodiment, system 10 of FIG. 1 can be an osmotic system. Osmotic system 10 comprises a module 11 formed of a solid body of polymer and drug. System 10 has a portal 12 of a predetermined area for releasing drug 13 to the tissue. Portal 12 is the single releasing surface unidirectionally dispensing drug 13 from osmotic system 10. Osmotic system 10 is comprised of about 15% to 90% by weight of discrete drug 13 depots of 0.1 to 250 microns, number average, in size of drug 13 that is an osmotically effective solute. Drug 13 depot is dispersed in about 10 to about 85% by weight of a polymer such that the depots are surrounded individually by a layer of polymer. The depots and polymer formed reservoir 15 of osmotic system 10. The polymer of osmotic system 10 is substantially impermeable to drug 13, but is permeable to water and biological fluid. Osmotic system 10 released drug 13 by fluid being imbibed by the depots in a serially inwardly manner causing the polymer layer surrounding the depots to rupture and release drug 13 at a controlled rate of release to the tissue.

In another embodiment, system 10 of FIG. 1 can be a bioerodible system. Bioerodible system 10 comprises a module 11, which module is a body formed of a bioerodible polymer that acts as reservoir 15 for housing drug 13. System 10 has a single portal 12 for releasing drug 13. Portal 12 additionally functions as a rate controller 12 as it bioerodes and releases drug 13 at a controlled rate of release over a prolonged period of time to the tissue.

Figure 4:
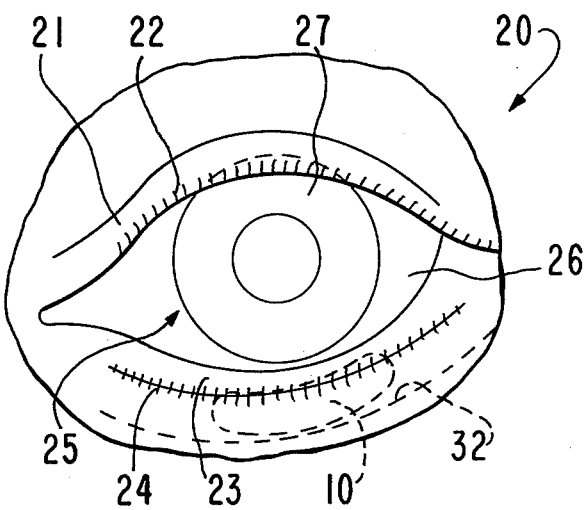
FIG. 4 is a view partly in frontal elevation and partly diagrammatic of a human eye further illustrating an ocular therapeutic system selectively releasing drug to a particular tissue of the eye placed for releasing drug thereto.
Figure 5:
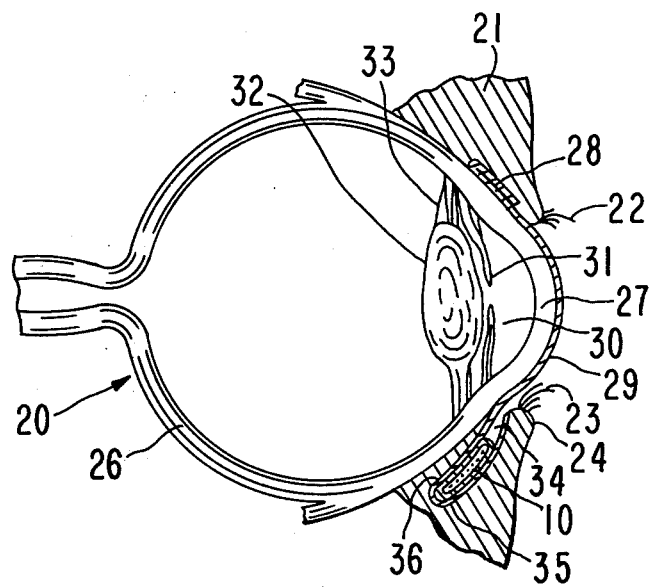
FIG. 5 is a side cross-section view of a human eye illustrating an ocular therapeutic system positioned in the lower cul-de-sac of the eye with the system dispensing medication to a single drug surface of the cul-de-sac.

Osmotic system 10, in all of the embodiments disclosed above, is manufactured as a platform sized, shaped and adapted for insertion and comfortable placement in the eye. The marginal outline of ocular system 10 can be ellipsoid, doughnut, bean, banana, circular, ring, crescent, rectangular, square, oval, tombstone, half-circle, and like geometric shapes. In cross-section, system 10 can be convex, doubly convex, concavo-convex, rectangular and the like. When in the eye, system 10 will tend to adapt the curvature of the part of the eye adjacent thereto, and the system will impart its shape to tear film present between system 10 and the selected drug receiving tissue of the eye. The dimensions of the ocular system can vary widely. The lower limit on the size of system 10 is governed by the amount of the particular drug 13 to be administered to elicit the desired pharmacologic or physiologic response, as well as the smallest sized system that can be conveniently inserted and maintained in the eye. The upper limit on the size of system 10 is governed by the geometric space limitations of the eye, consistent with the drug receiving tissue and comfortable insertion and retention in the eye. Satisfactory results can be obtained with ocular systems for insertion in the cul-de-sac of the eye of an adult human having a length of 2 to 20 millimeters, a width of 1 to 15 millimeters, and a thickness of 0.1 to 4 millimeters. Ocular system 10 is made of flexible materials that are non-allergenic to the eye and it is sized, shaped and adapted for insertion and comfortable placement in the eye of animals, including warm blooded mammals and humans. In a presently preferred embodiment, system 10 is designed for placement in the upper or lower cul-de-sac as seen in FIGS. 4 and 5. In the cul-de-sac, portal 12 of system 10 makes available the control of drug concentration in tissues and structure of the eye by controlling the area, the rate of release of drug per area, and specific direction of drug releasing surface of the portal, and by reducing dispersion of drug outside of the immediate drug releasing area of system 10.

Ocular system 10 can be used for the selective administration of drug to effect preselected drug therapeutic programs. The therapeutic program presents the drug in the most beneficial manner to the tissue compartment to produce the most beneficial effect. Generically, the therapeutic programs embrace the concept of continuous therapeutic coverage for a prolonged period of time, releasing the drug in a well-defined pattern. The pattern can be the release of drug at a constant rate, or the release of drug at varying rates, such as: (a) pulses including minutes to hours, days to weeks, weeks to months, one or two doses a day, one or two doses a week; (b) parabolic; (c) sinusoidal; (d) circadian; (e) multi-step, and the like.

In operation, when system 10 is in the eye, portal 12 is oriented towards a preselected tissue of the eye, while non-emitting surfaces of system 10 are oriented away from the preselected tissue. Portal 12 can be oriented to administer drug (a) internally to the eye, (b) to the interior surface of the eyelid, (c) to vascular areas for admitting drug into systemic circulation for producing an effect at a site remote from the eye, and (d) oriented for admitting drug to the nasopharyngeal, esophageal or throat area. Portal 12 of system 10 is in direct contact with the ocular tear film positioned therebetween. The thin tear film in the eye is simultaneously contiguous with the portal and the tissue requiring treatment, and it acts as a second drug reservoir by accepting drug from the portal for directly supplying and transferring drug to the tissue of the eye. The thin, fluid film between the portal drug emitting surface and the eye embraces dimensions corresponding to the size and shape of the drug emitting portal, and these dimensions remain substantially constant throughout the drug release period. The tear film thus becomes an integral component of drug delivery system 10. The tear film moves and acts in concert with the drug emitting portal and enhances system-to-biological membrane drug transfer with minimal lateral dispersion of drug.

Figure 2:
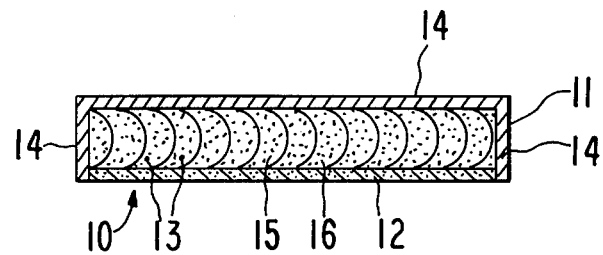
FIG. 2 is a cross-sectional view of an ocular therapeutic system manufactured with a reservoir containing drug with the reservoir surrounded by a membrane having a single side formed for emitting drug from the system.

In FIG. 2, there is seen another ocular therapeutic system 10 manufactured as a sealed container according to the mode and manner of the invention. System 10, as illustrated in FIG. 2, is shaped in the form of a rectangular ocular device 10 comprising a module 11, having a sole drug emitting portal 12 and other membranes 14 that are substantially impermeable to the passage of drug 13. Portal 12, in this embodiment also is the system's rate controller and portal 12 along with membrane 14 surround reservoir 15 containing drug 13. Reservoir 15 comprises a carrier 16 containing drug 13. Carrier 16 is formed of a release rate controlling material permeable to the passage of drug 13 by diffusion. The rate of passage of drug 13 through carrier 16 is higher than the rate of passage of drug 13 through controller-portal 12 so that release by controller-portal 12 is the release rate controlling step for releasing drug 13 from system 10. In operation, when system 10 is in the eye with portal 12 facing a tissue, drug 13 is administered by portal 12 unidirectionally releasing drug 13 into the adjacent thin eye fluid film positioned between portal 12 and the contacting drug receiving tissue of the eye for penetration into that part of the eye with minimal lateral dispersion of drug 13 in the eye. System 10 releases drug 13 at a controlled rate and pattern over a prolonged period of time to the tissue for producing the desired beneficial effect with much lower amount and at lower concentration of the drug. System 10, by delivering drug 13 from portal 12 to a facing, correspondingly shaped drug receiving tissue of the eye, avoids release of drug from the side of the system 10 distant from the drug receiving tissue thereby substantially lessening the distance drug must travel or diffuse to reach the tissue. This system and mode of administration results in a reduction of the amount of drug needed to achieve the desired effect.

Figure 3:
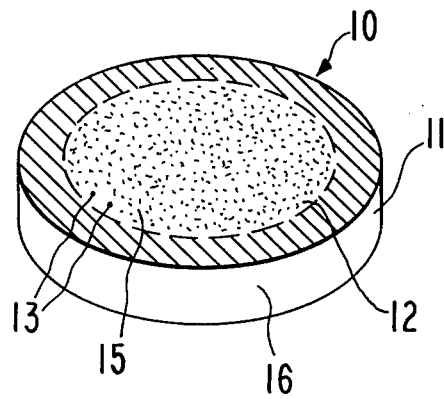
FIG. 3 is a top view of the cross-section of an ocular therapeutic system integrated into a unit manufactured as a platform shaped as an annular ring. The system has a drug reservoir and portal for releasing drug.

In FIG. 3 there is seen an ocular system 10 that diagrammatically illustrates another embodiment provided by the invention. System 10 of FIG. 3 comprises a module 11 having a drug emitting portal 12 and a wall 16 with both enclosing a reservoir 15 containing drug 13, and a carrier therefor. Portal 12 comprises a single surface of system 10 and it is formed of a material permeable to the passage of drug 13 as by diffusion. Wall 16 encapsulates the remainder of ocular system 10 and it is formed of a material substantially impermeable to the passage of drug 13. Ocular system 10 comprises portal 12 and wall 16 can in one embodiment be viewed as a sealed container having drug in the interior thereof, and it can be manufactured as a container having a circular or ellipsoidal cross-section. System 10 operates in the manner described supra. The system of FIG. 3 can be made to release drug 13 osmotically by using an osmotically effective drug, or by incorporating an osmotically effective solute along with drug into system 10. System 10 also can be made bioerodible in the manner described above. In both embodiments, drug 13 is released through a single unidirectional portal 12.

Referring to FIG. 4, ocular therapeutic system 10 is shown positioned in immediate contact with an eye 20 for administering a drug to a selected part thereof. Eye 20 comprises an upper eyelid 21 with eyelashes 22 at the edge of eyelid 21 and a lower eyelid 23 with eyelashes 24 at the edge of eyelid 23. Eye 20 anatomically comprises an eyeball 25 covered for the greater part of its posterior area by a sclera 26 and at its central area by cornea 27. Eyelids 21 and 23 are lined with an epithelial membrane or palpebral conjunctiva, not shown in FIG. 4, and sclera 26 is lined with a bulbar conjunctiva, not shown in FIG. 4. The portion of the palpebral conjunctiva which lines upper eyelid 21 and the underlying portion of the bulbar conjunctiva define as upper cul-de-sac, not seen in FIG. 4, while that portion of the palpebral conjunctiva which lines the lower eyelid 23 and the underlying portion of the bulbar conjunctiva define a lower cul-de-sac, not seen in FIG. 4. System 10 may be shaped and sized for insertion and placement in any part of the eye and in a presently preferred embodiment, system 10 is sized, shaped and adapted for insertion in the upper or lower cul-de-sac. In FIG. 4, system 10 is seen in broken continuous lines in the lower cul-de-sac, generally held in position by the natural pressure of the eyelid.

In FIG. 5, eye 20 is shown in side view in a horizontal section with system 10 positioned to dispense drug 13 to a selected part thereof. Eye 20 of FIG. 5 is comprised of an upper eyelid 21 with eyelashes 22, upper cul-de-sac 28, iris 31, cornea 27, tear film 29, aqueous humor 30, lens 32, ciliary muscle 33, lower eyelid 23, lower eyelashes 24, lower cul-de-sac 34 having a palpebral conjunctiva 35 and a bulbar conjunctiva 36 with each able to act as drug receptor tissue sites for specific drugs. System 10 is seen positioned in lower cul-de-sac 34 for continuous dispensing a predetermined amount of drug to either the bulbar conjunctiva 35 or the palpebral conjunctiva 36 for producing the desired therapeutic effect in the specific drug receiving site.

DETAILED DESCRIPTION OF THE INVENTION

In accordance with the practice of this invention, it has now been found that ocular therapeutic systems can be used to provide many important advantages and contributions for administering drug to certain drug receptor parts of the eye. For example, ocular therapeutic systems having improved drug delivery rate controlling membranes and pharmokinetics can be manufactured for use comprising a single drug emitting portal. The bioavailability of these systems have a release rate per unit area of drug emitting surface which in intimate contact with the drug receiving surface of the eye simultaneously enhances the direct administration of drug to the eye. For a given rate of drug delivered, the amount of drug transferred to the tissue compartments of the eye is in direct proportion to the area of the drug emitting portal. According to the invention, when treating tissues inside the eye it is possible to increase significantly drug bioavailability by having (a) only one portal of drug delivery oriented towards the bulbar conjunctiva and (b) maximizing the area of the drug emitting membrane or portal. These benefits are accomplished at lower dosage amounts and with minimal lateral dispersion of drug outside of the drug transfer, drug receiving locus of the system and the eye. Further, the ocular systems of the invention are designed for use to achieve fixed ocular space orientation in the ocular environment and they also are inventively designed with a specific drug delivery means to provide drug delivery with a high order of ocular receiving tissue specificity.

Materials suitable for fabricating system 10, its rate controller and portal, can be selected for diffusional systems from naturally occurring and synthetic materials that are biologically compatible with the eye, its fluid, and eye tissues, and they are essentially insoluble in eye fluids with which the materials will come in contact. The use of rapidly dissolving materials or materials highly soluble in eye fluid are to be avoided since dissolution of the wall would affect the constancy of the drug release, as well as the capability of the system to remain in place for a prolonged period of time. Suitable materials in one embodiment for forming the system or the drug emitting portal are homogenous materials permeable to the passage of drug by diffusion. Exemplary suitable materials for the fabrication purposes include ethylene-vinyl ester copolymers of the general formula:

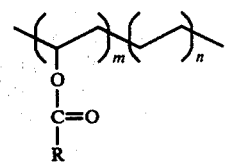

wherein R is hydrogen, lower alkyl of 1 to 7 carbons and aryl, and m is (4 to 80)% by weight and n is (100 - m)% by weight. Typical alkyl groups include methyl, ethyl, propyl, isopropyl, tert-butyl, pentyl and hexyl. Typical aryl groups include phenyl. Representative ethylene-vinyl ester copolymers, named as the acetates, include ethylene-vinyl formate, ethylene-vinyl acetate, ethylene-vinyl methylacetate, ethylene-vinyl ethylacetate, ethylene-vinyl propylacetate and the like. A preferred ethylene-vinyl ester copolymer includes ethylene-vinyl acetate having a vinyl acetate content of about 4 to 80% by weight of the total, a melt index of about 0.1 to 1000 grams per ten minutes, a density of 0.920 to 1.09, and a frequency of acetoxy groups on the polyethylene backbone of 1/150 to 1/3.5. Ethylene-vinyl ester copolymers including ethylene-vinyl acetate copolymers for the manufacture of diffusional ocular drug delivery devices are the invention of Takeru Higuchi and Anwar Hussain disclosed and claimed in United States Patent Application Ser. Nos. 705,470 and 705,479, both filed on July 15, 1976 and assigned to the ALZA Corporation of Palo Alto, Calif. Ethylene-vinyl ester copolymers are commercially available and they are described in U.S. Pat. Nos. 2,200,429; 2,396,785 and 2,947,735; and British Pat. Nos. 569,927 and 582,093; and in Crystalline Olefin Polymers, edited by Raff, R. A. V. and Doak, D. W., Part II, pages 261 to 266, 1964, published by Interscience Publishers, New York. Additional exemplary materials suitable for manufacturing the system include poly(methylmethacrylate), poly(butylmethacrylate), plasticized poly(vinylchloride), plasticized poly(amides), plasticized soft nylon, plasticized poly(ethylene terephthalate), poly(isoprene), poly(isobutylene), poly(butadiene), poly(ethylene), poly(tetrafluoroethylene), poly(vinylidene chloride), poly(acrylonitrile), cross-linked poly(vinylpyrrolidone), poly(trifluorochloroethylene), chlorinated poly(ethylene), poly(4,4'-isopropylidene diphenyl carbonate), plasticized ethylene-vinyl acetate copolymer, vinylidene chloride-acrylonitrile copolymer, vinyl chloride-diethyl fumerate copolymer, poly(dimethylsiloxane), ethylene-propylene copolymer, silicone-carbonate copolymers, vinylidene chloride-vinyl chloride copolymers, vinyl chloride-acrylonitrile copolymers, vinylidene chloride-acrylonitrile copolymers, and the like.

Microporous materials suitable for fabricating the drug system 10, rate controller 12, portal 12 and reservoir 15 include polymers having a pore size of several angstroms, usually at least 10 Å to several hundred microns. The porosity of these materials range from about 5% to about 95%. The microporous materials are capable of housing in their micropores a medium permeable to the passage of drug by diffusion. Exemplary microporous materials include cellulose, acylated cellulose, esterified cellulose, cellulose acetate propionate, cellulose acetate diethyl aminoacetate, poly(urethane), poly(carbonate), microporous polymers formed by the coprecipitation of a polycation and a polyanion as disclosed in U.S. Pat. Nos. 3,276,589; 3,541,005; 3,541,006; and 3,546,142; modified insoluble collagen, cross-linked poly(vinyl alcohol) with a pore size of 7 Å to 50 Å, poly(olefins) or poly(vinyl chlorides) with a pore size of about 50 Å or less to 150 microns or larger. Also, the materials that can be used include those materials having homogenous properties and microporous properties, such as cross-linked gelatinous membranes.

The diffusive media for use with the microporous materials are those media that are non-toxic in the eye and in which the drug has limited solubility and release the drug by diffusion. By "limited solubility" as used herein is meant the drug is soluble in a given amount of the diffusive medium and this includes solubilities such as soluble, sparingly soluble, slightly soluble, very slightly soluble and almost practically insoluble. Generically, the term comprises a range of solubility of drug in the medium of from 10 parts per million to 10,000 parts per million on a weight base. The medium can be a liquid, a gel, a colloidal solution, a sol, and the solution can be polar, semi-polar or non-polar. Representative mediums include saline, glycerine, ethylene glycol, propylene glycol, water, eye fluid, emulsifying and suspending agents such as methyl cellulose mixed with water, mixtures of propylene glycol monostearate and oils, gum tragacanth, sodium alginate, poly(vinyl pyrrolidone), poly(oxyethylene stearate), fatty acids such as linoleic, silicone oil, and the like. Representative mediums are set forth in Pharmaceutical Sciences, by Remington, pages 246 to 269 and 1338 to 1380, 1970, published by Mack Publishing Co., Easton, Pa.

Typical polymeric materials for forming the osmotic systems include materials known to the art as osmosis and reverse osmosis membranes, such as commercially available cellulose acetate and its derivatives, partial and completely hydrolyzed ethylene-vinyl acetate copolymers, highly plasticized polyvinyl chloride, homo- and copolymers of polyvinyl acetate, polyesters of acrylic acid and methacrylic acid, polyvinyl alkyl ethers, polyvinyl fluoride; silicone polycarbonates, aromatic nitrogen-containing polymeric membranes that exhibit water permeability and essentially no solute passage, osmosis membranes made from polymeric epoxides, osmosis membranes made from copolymers of an alkylene oxide and alkyl glycidyl ether, semipermeable polyurethanes, semipermeable polyglycolic or polylactic acid and derivatives thereof, the membranes of ionically associated polyelectrolytes, the polymers formed by the coprecipitation of polycation and polyanion as described in U.S. Pat. Nos. 3,173,876; 3,276,586; 3,541,005; 3,541,006; and 3,546,142, derivatives of polystyrene such as poly(sodium styrenesulfonate) and poly(vinyl benzyltrimethyl-ammonium chloride), and the like. Ethylene-vinyl acetate copolymers are especially useful for forming the osmotic system. Ethylene-vinyl acetate copolymer used for the manufacture of osmotic releasing ocular devices is the invention of Alan S. Michaels and Mark Gulloid as disclosed and claimed in United States Patent Application Ser. No. 578,979 filed on May 19, 1975, and assigned to the ALZA Corporation of Palo Alto, Calif. Preferred among the ethylene-vinyl acetate copolymers are those having a melt index above about 20 g/min and a vinyl acetate content above about 20%, such as from 20% to 45%. Preferred materials may be further described by their water-permeabilities, tensile strengths and maximum elongations. Preferred materials are water-insoluble materials having water permeabilities of from $10^{-8}$ to $10^{-12}$ gm.cm/cm$^2$sec.cm Hg and preferably in the range of $5 \times 10^{-9}$ to $5 \times 10^{-11}$ gm.cm/cm$^2$.sec.cm Hg (as determined by vapor cup permeability tests per a modified version of ASTM E 96) tensile strengths of from 400 to 10,000 psi, preferably 500 to 3,000 psi, and maximum elongations of from 10% to 2000%, preferably 200% to 1700%, while additionally possessing a high degree of impermeability to the drug.

Exemplary bioerodible materials suitable for manufacturing system 10 include polyesters of the general formula —O—(W)—CO— and mixtures thereof, wherein W is a lower alkylene of 1 to 7 carbons and in a presently preferred embodiment includes a member selected from the group of alkylenes of the formula —CH$_2$—, or —CH—CH$_2$—, and Y has a value such that the molecular weight of the polymer is from about 4,000 to 100,000. The polymers are polymerization-condensation products of monobasic hydroxy acid of the formula $C_nH_{2n}(OH)COOH$ wherein n has a value of 1 to 7, preferable 1 or 2, and the acid is especially lactic acid or glycolic acid. Also included are copolymers derived from mixtures of these acids. The preparation of polymers of the formula above forms no part of the present invention. Several procedures are available and reported by Filachione, et al, Industrial and Engineering Chemistry, Volume 36, No. 3, pages 223 to 228, March 1944, Tsuruta, et al, Macromol. Chem., Volume 75, pages 211 to 214, 1964, and in U.S. Pat. Nos. 2,668,162; 2,703,316; 2,767,945; 3,297,033. These polymers are hydrophobic and substantially impermeable to drugs. Bioerodible materials also include poly(orthoesters). These materials have the following general formula:

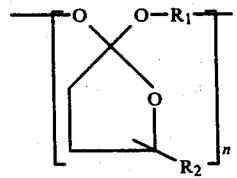

wherein $R_1$ is an alkylene of 4 to 12 carbons, a cycloalkylene of 5 to 6 carbons substituted with an alkylene of 1 to 7 carbons and an alkyleneoxy of 1 to 7 carbons, and R$_2$ is a lower alkyl of 1 to 7 carbons. The polymers also include the cis,trans, the cis/trans forms and the block and random copolymers. The polyorthoesters used for the manufacture of ocular drug delivery devices releasing drug by bioeroding are the invention of Nam Choi and Jorge Heller disclosed and claimed in United States Patent Application Ser. No. 544,808 filed Jan. 28, 1975, which application is assigned to the ALZA Corporation of Palo Alto, Calif. The poly(orthoesters) are known in Belgium Pat. No. 837,935, Netherland patent No. 7,600,881 and West German No. 2,602,994.

Materials suitable for forming membranes or walls of system 10 that are impermeable to drug are naturally occurring or synthetic materials impermeable to drug, or a material permeable to drug which material carries on its surface a different material that is impermeable to the passage of drug. For this purpose, any of the above-described materials that possess this particular property for a given drug may be used for this structure. That is, in manufacturing the ocular system, a material permeable to the passage of a given drug is selected for forming the system, rate controller, etc, and then a material impermeable to the passage of the same drug is selected to form the non-emitting surfaces of the system. Detailed methods for selecting both permeable and impermeable materials are presented later in the disclosure.

As used for the purpose of this invention, the term "drug" embraces any drug that can be administered by the ocular system 10 to the drug receptor site of the eye to produce a local or a systemic physiologic or pharmacologic beneficial effect, according to the specific method of release of the invention. The local effect can be produced internally in the eye, or the local effect can be produced at a specific site in the eye cavity, for example on the interior surface of the upper or lower eyelid. The systemic drug is introduced into the circulatory system to produce a beneficial effect at a site remote from the eye. Exemplary drugs include antibiotics such as tetracycline, chlortetracycline, bacitracin, neomycin, polymyxin, gramicidin, cephalexin, oxytetracycline, chloramphenicol, kanamycin, gentamycin, erythromycin and penicillin; antibacterials such as sulfonamides, sulfadiazine, sulfacetamide, sulfamethiazole and sulfisoxazole, nitrofurazone and sodium propionate; antivirals including idoxuridine and interferon; antiallergenics such as antazoline, methapyriline, chlorpheniramine, phyilamine and prophenpyridamine; anti-inflammatories such as hydrocortisone, hydrocortisone acetate, dexamethasone, dexamethasone 21-phosphate, fluocinolone, medrysone, prednisolone acetate, fluoromethalone, betamethasone, and triaminolone; deconges-tants such as phenylphrine, naphazoline and tetrahydrozoline; miotics and anticholinesterase such as pilocarpine, physostigmine, eserine, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphentamine; sympathoimimetics such as ephinephrine; immunological drugs such as vaccines and immune stimulants; and hormonal agents such as estrogens, estradiol, progestational, progesterone, insulin, calcitonin, parathyroid hormone and peptide, vasopressin, hypothalmus releasing factor; and other drugs such as prostaglandins, antiprostaglandins, and prostaglandin precursors. Drugs used in osmotic systems are preferrably present in an osmotically effective form such as ephedrine hydrochloride, ephedrine sulfate, pilocarpine hydrochloride, pilocarpine nitrate, calcium pantotheate, prednisolone sodium phosphate and the like. The above drugs, and other locally and systemically acting drugs, and their effective dose coupled with other physiological and pharmacological information are described in Physicians Desk Reference, Drug Classification Index, and entries cited thereon, 24th Edition, 1969, published by Medical Economics, Inc., Oradell, New Jersey; in Handbook or Ocular Therapeutics and Pharmacology, by Ellis and Smith, pages 159 to 240, 1973, published by C. V. Mosby Co., St. Louis, Mo., and in The Pharmaceutical Bases of Therapeutics, by Goodman and Gilman, 14th Edition, 1970, published by the Macmillan Co., London. The drugs administered from the ocular system can be in various diffusional forms such as esters, ethers, amides, and the like, which have desirable retention, release or solubility characteristics, and which are easily hydrolyzed by body pH, enzymes or metabolic processes, can be used for the purpose of the invention.

The amount of drug contained in an ocular system 10 is determined by that amount sufficient to maintain the desired dosage level over the therapeutic treatment period. Typically, from 25 micrograms or less to about 2000 milligrams or more of drug can be incorporated into system 10 with the exact amount depending upon the drug and the treatment period. For example, in order to administer drug internally to treat glaucoma in an adult human, the daily released dosage from a unidirectional drug emitting portal of an ocular system will range from 100 micrograms to 20,000 micrograms of pilocarpine per day. Thus, using pilocarpine with a system intended to remain in place for 7 days and with a release rate of 20 micrograms per hour or 480 micrograms per day, at least 3.5 milligrams of pilocarpine will be incorporated into the ocular system. Other systems containing different kinds and amounts of drugs for use for different therapies and time periods and for releasing the drug at lower or higher controlled rates also are readily provided for specific release by this invention.

The osmotically effective solutes that can be added to an osmotic system include water-soluble inorganic and organic salts and compounds such as magnesium sulfate, magnesium chloride, sodium chloride, lithium chloride, potassium sulfate, sodium carbonate, sodium sulfate, lithium sulfate, calcium bicarbonate, sodium sulfate, calcium sulfate, potassium acid phosphate, calcium lactate, magnesium succinate, tartaric acid, acetamide, choline chloride, soluble carbohydrates such as sorbitol, mannitol, raffinose, glucose, sucrose, lactose, mixtures thereof and the like.

The reservoir of ocular system 10 in the embodiment of the invention using a reservoir, is a matrix that contacts the inner surface of the drug rate controller and supplies drug thereto. The reservoir is comprised of a liquid, gel, colloid, film, semi-solid or solid matrix or carrier containing drug, homogenously or heterogenously dispersed and/or dissolved therein. Carrier 16 is permeable to the passage of drug by diffusion. Carrier 16 can be hydrophobic, hydrophilic, organic, inorganic, naturally occurring or a synthetic material. Exemplary carrier-forming materials are gelatin, starches, carbohydrates such as gel-forming agar, agarose, algin, sodium alginate, potassium alginate, carrageen, kappa-carrageenan, lambda-carrageenan, fucordan, fucellaran, laminaran, hypnea, gum arabic, gum ghatti, gum karaya, gum tragacanth, guar gum, Irish moss, hydrophilic hydrogels of esters of acrylic acid, modified collagen, synthetic gel formers such as methylcellulose, hydroxyalkyl derivatives of cellulose wherein the alkyl is 1 to 7 carbons, ethylhydroxyethylcellulose, and sodium carboxymethylcellulose. Also, other commercially available matrix forming materials permeable to the passage of drug but at a higher rate of passage than through the membrane of the system are suitable for forming the reservoir of the system. Representative matrixes are set forth in Pharmaceutical Sciences, by Remington, pages 246 to 269, 1338 to 1390 and 1627 to 1979, 1970, published by Mack Publishing Co., Easton, Pa.

Selection of the particular material for forming the rate controller 12 is governed in large part by the drug to be incorporated in the system, as well as by the desired rate of release of the drug. Those skilled in the art can readily determine the rate of diffusion of drugs through homogenous imperforate polymers and copolymers and select suitable combinations of a polymer or copolymer and drug for particular applications. Various techniques can be used to determine the permeability of the polymers and copolymers to different drugs. One that has been found to be eminently well-suited is to cast or hot press a film of the polymeric material to a thickness in the range of 2 to 60 mils. The film is used as a barrier between a rapidly stirred (e.g., 150 r.p.m.) saturated solution of the drug and a rapidly stirred solvent bath, both maintained at constant temperature (typically 37° C.). Samples are periodically withdrawn from the solvent bath and analyzed for drug concentration. By plotting drug concentration in the solvent bath versus time, the permeability constant P of the film is determined by the Fick's First Law of Diffusion.

$$\text{Slope of plot} = \frac{Q_1 - Q_2}{t_1 - t_2} = P \frac{AC}{h}$$

wherein $Q_1$=cumulative amount of drug in solvent in micrograms at $t_1$; $Q_2$=cumulative amount of drug in solvent in micrograms at $t_2$; $t_1$=elapsed time to first sample, i.e., $Q_1$; $t_2$=elapsed time to second sample, i.e., $Q_2$; A=area of film in cm$^2$; C=initial concentration of drug in saturated solution at t; h=thickness of film in cm. By determining the slope of the plot, i.e., $$\left[\frac{Q_1 - Q_2}{t_1 - t_2}\right],$$

and solving the equation using the known or measured values of A, C, and h, the permeability P constant in cm$^2$/time of the film for a given drug is readily determined. Of course, this permeability constant is an inherent characteristic of a polymer or copolymer of particular composition and melt index, and is unchanged whether the material is used as a matrix or as a film releasing membrane. The procedures used to determine the rate of drug release through a polymer or copolymer also can be used to determine if a material is impermeable to drug. These procedures are standard techniques known to the art as recorded in J. Pharm. Sci., Vol. 52, pages 1145 to 1149, 1963; ibid., Vol. 53, pages 798 to 802, 1964; ibid., Vol 54, pages 1459 to 1464, 1965; ibid., Vol. 55, pages 840 to 843, and 1224 to 1239, 1966; Encyclopedia Polymer Science Technology, Vols. 5 and 9, pages 65 to 82, and 794 to 807, 1968; the references cited therein, and the like.

The rate of release of a drug through various diffusive materials in the pores of the microporous wall can be easily determined by those skilled in the art by standard procedures, as described in Encyclopedia Polymer Science Technology, Vols. 5 and 9, pages 65 to 82, and 794 to 807 1968; and the references cited therein; in Membrane Science and Technology, by Flinn, James E., pages 16 to 32 and 120 to 138, 1970, published by Plenum Press, Inc.; and in Chemical Engineers Handbook, pages 17-42 to 17-45, 1963, published by McGraw Hill, Inc. One applicable method employs Fick's First Law of Diffusion, wherein the flux of drug through a convection-free medium, for example, a liquid present in a porous membrane, is given by the equation;

$$J = \frac{-\epsilon D}{T} \frac{dc}{d\chi}$$

wherein J is the flux in gm/cm$^2$ sec., $\epsilon$ is the porosity in cm$^3$/cm$^2$, T is the tortuosity factor, D is the diffusion coefficient cm$^2$/sec., and dc/dx is the drug concentration gradient across the barrier. Thus, when the diffusion coefficient is assumed to be independent of concentration, and the concentration at the outside surface is negligibly small, the equation can be expressed as follows:

$$J = \frac{\epsilon D}{T} \frac{C_s}{l}$$

wherein $C_s$ is the saturation solubility of the drug in the diffusive medium, and l is the barrier thickness. The diffusion coefficient D will be in the order of $2 \times 10^{-6}$ cm$^2$sec$^{-1}$ when the drug has a small molecular diameter, for example, about 10 Å and the pore diameter of the microporous membrane is large in comparison with the molecular drug diameter, for example, at least greater by a factor of 10. However, when the pore diameter of the rate controlling membrane 12 is reduced relative to that of the molecular drug diameter, for example, from 10 to about 3 times the molecular diameter, the diffusion coefficient D will decrease to values as low as $2 \times 10^{-8}$ cm$^2$sec$^{-1}$. When the ratio of membrane 12 pore diameter to molecular drug diameter significantly is below about 3, the membranes are considered to be homogeneous solution diffusion materials. By varying pore diameter or porosity of the microporous materials, substantial changes in release rate can be brought about while still using the same materials.

The diffusion coefficient of a drug is determined by measuring the rate a drug transfers from one chamber through a sintered glass filter of known pore size and thickness into another chamber and calculating from the obtained data the drug transfer rate. The method when used for a diffusive medium, is carried out by adding to a first conical flask equipped with a ground glass stopper and a stirring bar, a measured amount of medium and simultaneously, the drug in the same medium is added to a second conical flask while keeping the level of the medium in the two flasks the same. Next, the flasks are stirred, the samples drawn at various time intervals for analysis. The measured rate of drug transport through the sintered glass filter, and the concentration difference of the drug in the two flasks is then calculated. These procedures are known to the art in Proc. Roy. Sci. London, Ser. A, Vol. 148, page 1935; J. Pharm. Sci., Vol. 55, pages 1224 to 1229, 1966 and references therein. The diffusion coefficient of a drug in the solid carrier also can be experimentally determined by using the above apparatus or similar apparatus and procedures as described in Diffusion in Solids, Liquids and Gases, by Jost, W., Chapter XI, pages 436 to 488, 1960, Revised Edition, Academic Press, Inc., New York.

The solubility, or insolubility, of drug in a membrane or carrier is determined by preparing a saturated solution of drug and ascertaining, by analysis, the amount present in a measured area of the membrane or carrier. For example, the solubility of drug in a polymer or carrier is determined by first equilibrating the material with a saturated solution of the drug at a known temperature, for example 37° C., or with a pure liquid drug, if the drug is a liquid at 37° C. Next, drug is desorbed from the saturated material with a suitable solvent for the drug. The resultant solution is analyzed by standard techniques such as ultraviolet, visible spectrophotometry, refractive index, polarography, and electrical conductivity, and from data calculating the concentration, the solubility or insolubulity of the drug in the polymeric material.

The solubility of a drug in a diffusive medium in the pores or in another vehicle can be determined by art known techniques. One method consists in preparing a solution of the drug and ascertaining by analysis the amount of drug present in a definite quantity of the medium. A simple apparatus for this purpose consists of a test tube fastened upright in a water bath maintained at constant temperature. The medium and drug are placed in the tube and stirred by a motor driven rotating glass spiral. After a given period of stirring, a known weight of the medium is analyzed and the stirring continued for an additional period of time. If the analysis shows no increase of dissolved substance after the second period of stirring, the results are taken as the degree of solubility of the drug in the medium. Numerous other methods are available for the determination of the degree of solubility of a drug in a liquid medium. Typical methods used for the measurement of solubility are chemical analysis, measurement of density, refractive index and electrical conductivity. Details of various methods for determining solubilities are described in United States Public Health Service Bulletin No. 67, of the Hygenic Laboratory, Encyclopedia of Science and Technology, Vol. 12, pages 542 to 556, 1971, McGraw Hill, Inc.; Encyclopedic Dictionary of Physics, Vol. 6, pages 545 to 557, 1962, Pergamon Press, Inc., and the like.

The rate of solubilization, or insolubilization, or the rate at which drug will go into solution or dissolve in the reservoir or vehicle confined therein, is quantitatively governed by known physico-chemical principles. For an example, a drug particle dispersed in a material is surrounded by a thin layer of material having a finite thickness l in cm. This layer is considered as an integral part of the drug and it is characteristically referred to as the "stagnant layer". The stagnant layer remains a part of the surface of the drug, moving whenever the drug moves. Using Fick's First Law of Diffusion, the rate of solution is the rate at which a dissolved drug diffuses through the stagnant layer for supplying drug to the drug device's reservoir's inner wall. The driving force behind the movement of the drug through the stagnant layer is the difference in concentration of the drug, $C_1$, in the stagnant layer at the surface of the drug, and the concentration $C_2$ on the farthest side of the stagnant layer. The difference in concentration $C_1-C_2$ determines the rate at which drug is solubilized in the vehicle. Hence, if the material on the farthest side contains its optimum concentration because of a low release by the drug release rate controlling wall, the rate of solubilization of new drug will be low. Correspondingly, as drug leaves the vehicle, new drug is solubilized to establish a steady state within the vehicle.

Also, according to Fick's Law, the rate of drug solution and insolubility is directly proportional to the area of the drug, A in cm², as exposed to vehicle and inversely proportional to the length of the path through which the dissolved drug molecule must diffuse. Then, the rate of solution of the drug is given by:

$$R = \frac{DA}{l}(C_1 - C_2)$$

wherein R is the rate of solution, D is a proportionally constant called diffusion coefficient in cm²/sec, and $C_1$, $C_2$, and l are as previously defined. See Remington's Pharmaceutical Science, 14th Ed., pages 246 to 269, 1970, Mack Publishing Co.

Permeability and impermeability of polymers and copolymers to drugs by diffusion also can be varied by incorporating fillers into the polymers and copolymers. Typical fillers that can be employed in practice of the invention are silica, clay, barytes, carbon black, lithopone, zinc oxide, etc. It should be realized that use of many of these fillers will affect the melt index of the polymer or copolymer. By varying the composition, the filler and thickness of the rate controlling membrane, the dosage rate per area of the membrane can be controlled to meter the diffusion of drug to the exterior of the system. Thus, systems of the same surface area can provide different dosage of a drug by varying the characteristics of the polymer or copolymer.

System 10 manufactured in the form of unit, integrated devices are easily fabricated. When system 10 is in the form of a matrix with drug distributed therethrough, the particles of the drug can be mixed with the polymer or copolymer, which can be in the solid, semisolid, or liquid form at the time, and distributed therethrough by ballmilling, callendering, stirring, shaking or the like. Where the drug is chemically compatible with the monomers used to form the polymer or copolymer, the drug can be added at this earlier stage and the matrix formed in situ. The matrix, however made and having the drug distributed therethrough, can then be formed to a solid shape by molding, casting, pressing, extruding, drawing or like processes. Thereafter, the matrix can be cross-linked, if desired, for example by using irradiation. Alternatively, the matrix can be formed to the desired shape and placed in a bath of the drug or of a solvent solution of the drug which then diffuses into the matrix to provide system 10. When system 10 is a sealed container with a membrane of a polymer or copolymer and the drug in an interior reservoir, the container can be fabricated in many ways. Preformed hollow shapes of polymer or copolymer such as tubing, can be filled with drug, alone or dispersed in a suitable vehicle, and the ends sealed with plugs or by heat to form a system that is partially coated with an impermeable material. Alternatively, the drug can be laminated between sheets of the polymer or copolymer which can be sealed together with adhesive or by heat, wherein only one sheet is formed of a material permeable to drug. Other encapsulation, bonding and coating techniques conventionally used in the art can be employed. The ability to shape the polymer into tubes, disks, films, rings and another highly reproducible shapes of controllable composition results in ready fabrication of systems with closely controlled characteristics that overcome the significant disadvantages of previously described ocular systems. Other standard procedures, as described in Modern Plastics Encyclopedia, Volume 46, pages 62 to 70, 1969, published by McGraw Hill, Inc., well known to those skilled in the art can be used to fabricate the drug delivery systems of the invention.

DESCRIPTION OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, drawings, and the accompanying claims.

EXAMPLE 1

An ocular drug dispensing system of elliptical shape and comprised of one outer drug release rate controller membrane which also serves as portal member No. 1 and one outer membrane impermeable to drug member No. 3 are fused to an inner middle thin member No. 2 having a center opened area defining a space occupied by drug carrier reservoir and which middle film member No. 2 extends around and interbonds the perimeter of the two outer facing members Nos. 1 and 3 to form an ocular drug dispensing system is manufactured as follows: first, a uniform membrane is formed by dissolving commercially available ethylene-vinyl acetate copolymer having an acetate content of 40% in methylene chloride in a concentration ratio of 20% copolymer to 80% solvent and film casting the solution onto a glass substrate. This membrane forms the rate controller and the portal member No. 1 of the system. The solvent is allowed to evaporate at room temperature and the film warm air dried to yield a film about 1.7±0.2 mils thick. Two membranes, about 16 mm×6.75 mm, are cut out from the membrane, one of which will be used as the drug release membrane, member No. 1 of the ocular system, and the other to be laminated with a drug impermeable material. Next a middle film, member No. 2 is prepared by mixing ethylene-vinyl acetate copolymer, methylene chloride and Food Drug and Cosmetic blue lake dye of optionally titanium oxide, in a present ratio of 20 to 80 to 0.1 and the ingredients thoroughly mixed in a commercial, laboratory V-blender. The mixture is cast onto a glass surface, and the solvent evaporated at room temperature. Then the film is warm air dried to yield a film 4.2±0.3 mils thick. Next, this film is press-cut into an ellipse having the same dimension of the just press-cut membranes. The middle film is press-cut with the center area punched out to yield a continuous ellipsoidal ring defining an opening. Then onto the drug release membrane, member No. 1, is placed in the middle ellipsoidal center ring and these two members are placed into a conventional standard volume laminator. Next, a vacuum is pulled to 74 cm of mercury and held for three minutes. At the end of the three minutes, a high flux radiant heater is positioned over the members and heated for about 15 seconds or until the temperature reaches about 70° C. At the end of the heating, a pressure head is applied to the members and a pressure of 6.8 Kg applied for 45 seconds to firmly seal the two members, and the vacuum released.

Next, to 500 grams of sterile, distilled water is added 300 grams of pilocarpine base and 25 grams of alginic acid and the ingredients well-mixed in a standard V-blender. Following the mixing, the mixture is cast on a clean glass plate. The water is evaporated at room temperature to yield an alginic acid-pilocarpine drug carrier, of approximately 92.3 pilocarpine base and 7.7% alginic acid. The process uses a specific die of ellipse shape for cutting the drug center film; such ellipse being of precisely the same surface area and shape as the center space of the ellipsoidal ring comprising member No. 2 of the ocular system. A 7.0±0.1 mg aliquot of the drug carrier is then deposited into the two member laminate, and then membrane No. 3 placed in contact with the middle film No. 2. The three members are then vacuum heat laminated as just described.

Next, one membrane of the system is laminated with a layer of butyl rubber impermeable to the passage of pilocarpine to produce impermeable member No. 3 as follows: first, a 10% by weight solution comprising butyl rubber and titanium dioxide in chloroform was prepared by milling 5% by weight of titanium dioxide into 28.5 grams of butyl rubber to make a 30 gram dispersion. To this was added 270 grams of chloroform and the ingredients mixed until they were dissolved into a homogenous preparation. This solution was cast into a siliconized polyester film and allowed to dry at room temperature, under vacuum for 18 hours with 30 inches of Hg, also at room temperature. A group of the above ocular therapeutic systems were placed on a siliconized polyester film and the butyl rubber titanium dioxide film placed on the systems. A heated hot plate, about 80° C., was placed on the film for three minutes to laminate the impermeable film to one membrane of the system producing member No. 3 and ocular systems having a single drug emitting surface member No. 1. These systems when placed into an adult human's eye with the portal No. 1 facing the bulbar conjunctiva will administer 10 micrograms of pilocarpine per hour for 7 days to the tissues inside the eyeball. The drug emitting portal, surface No. 1 of the systems measured 13.4 mm by 5.7 mm.

EXAMPLE 2

An ocular drug delivery system for releasing pilocarpine at a controlled rate of 20 micrograms per hour was prepared by repeating the procedure of Example 1. All the conditions are as described except the rate controller, which in this embodiment also is the drug emitting portal, was formed from a composition comprising 80% ethylene-vinyl acetate copolymer having an acetyl content of 40% and 20% diethylhexyl phthalate. The drug releasing emitting surface of the system measured 13.4 mm by 5.7 mm or internally admitting pilocarpine to the preselected tissue compartment of the eye.

EXAMPLE 3

An ocular drug delivery system for releasing pilocarpine at a controlled rate of 40 micrograms per hour for 7 days was prepared by repeating the procedure of Example 1. The drug releasing membrane for the system of this example comprised 80% ethylene-vinyl acetate copolymer having an acetyl content of 40% and 20% diethylhexyl phthalate. The releasing surface of the system measured 16.0 mm by 6.75 mm.

EXAMPLE 4

An ocular drug delivery system for the controlled delivery of drug administration over a prolonged time is manufactured from drug release rate controlling material insoluble in eye fluid according to the procedure as described in Example 1 with the drug reservoir in this embodiment comprising pilocarpine and alginic acid, wherein the ratio of pilocarpine to alginic acid is from 12 to 1 and from 3 to 1 for the controlled release of the drug to the tissue compartment of the eye.

EXAMPLE 5

An ocular system for the prolonged administration of drug is made according to the procedures of Examples 1 and 4 with the pilocarpine alginic acid film prepared as follows: first, pilocarpine-free base is dissolved in freshly prepared deionized water. To this is added a stoichiometric amount of alginic acid and the mixture stirred until a viscous, homogenous solution is obtained. An excess of pilocarpine is then added and the solution cast onto a glass plate, doctor-bladed to the desired thickness and dried at room temperature. The transparent elastic and flexible film can be easily peeled from the glass and handled as needed. Films having an alginic acid to pilocarpine ratio of 1 to 12 are prepared, punched to fit inside the reservoir, and then the second barrier film laminated to the assembly.

EXAMPLE 6

An ocular therapeutic system comprising a drug emitting portal formed of ethylene-vinyl acetate copolymer having positioned thereon a pre-punched colored ethylene-vinyl acetate copolymer membrane with an inwardly disposed hole for receiving a pilocarpine polysaccharide film machine punched to fit inside the hole are placed on the platten in a laminator machine. The machine is closed and a vacuum equivalent to 29 inches of Hg is held for three minutes. At the end of three minutes, a radiant heater is turned on and allowed to warm up for 15 seconds. The heater is then positioned between the plattens and the surface of the film heated to 70° C. heated to 70° C. The heater is then removed and the plattens are pushed together, with approximately 30 pounds of force. The plattens remain together under pressure of 30 pounds for 45 seconds while the film cools. The vacuum is then released and the plattens returned to their original position. Then, the machine is opened, the pilocarpine polysaccharide solid film deposited in the cavity and a film of pilocarpine impermeable polytetrafluoroethylene placed over the exposed surface of the second membrane. The three membranes are returned to the laminator and the process repeated to yield the finished laminate ocular system having one surface permeable to the passage of pilocarpine and one surface impermeable to the passage of pilocarpine.

EXAMPLE 7

The procedure of Example 6 is repeated in this example with all conditions as described except the polysaccharide gellation agent is replaced with the following polysaccharide filmation agents: agar, agarose, kappa-carrageenan and hypnean.

EXAMPLE 8

Following the procedure set forth in Example 1, an ocular drug delivery system shaped like a circle 6 mm by 2.5 mm is prepared according to the described procedure except one of the membrane is formed from commercially available laminate of cellulose acetate and nylon-66 that is substantially impermeable to the passage of hydrocortisone alcohol in the reservoir of the system. The area of the system is 1 $cm^2$, and the membranes are 2 mils thick. The drug release rate for the ethylene-vinyl acetate copolymer film which is permeable to the steroid is about 40 micrograms per hour, and the release rate for the laminate cellulose acetate nylon is about 1 to 2 micrograms per hour.

EXAMPLE 9

An ocular drug delivery system having a banana shape and dimensions of 21 mm by 5 mm by 0.25 mm for administering a drug over a prolonged period of time at a controlled and continuous metered rate, is prepared as follows: a drug carrier mix is first prepared by mixing liquid polydimethylsiloxane with 200 micrograms of hydrocortisone alcohol and stannous octoate catalyst, 0.5% by weight, with the mixture charged into a pre-shaped banana mold having dimensions that correspond to the reservoir area of the ocular system. The drug-steroid carrier is allowed to cure at room temperature and then removed from the mold. Next, the drug-steroid is placed into the reservoir area of an ocular system comprised of a microporous cellulose acetate membrane having bonded onto its internal surface at the edge thereof, one side of poly-dimethylsiloxane banana-shaped ring. Then, a film of substantially steroid impermeable crosslinked polyamide is heat sealed under vacuum and pressed onto the exposed free surface of the opened ring to yield the ocular system. The microporous cellulose acetate membrane is characterized by a porosity of 60%, a pore size of 0.45 microns and a thickness of 4 mils. When inserted in the cul-de-sac of the conjunctiva between the sclera of the eyeball and the lower lid, with the microporous membrane oriented towards the internal surface of the eyelid, the system delivers steroid at a controlled and therapeutically effective rate to the lid for 24 hours of treatment.

EXAMPLE 10

Pilocarpine oil (200 milligrams) is placed between a film of ethylene-vinyl acetate copolymer and a film of pilocarpine impermeable polytetrafluoroethylene each having a thickness of 0.004 inches. The ethylene-vinyl acetate copolymer has a vinyl acetate content of 40% by weight and a melt index of 22 grams per ten minutes. Ellipsoidal ocular systems having a length of 1.3 cm, a width at their widest point of 4 mm, and a thickness of 0.5 mm, are heat stamped from the assemblage, with each system containing 2 milligrams of pilocarpine. These ocular systems can be inserted and retained in the cul-de-sac of the conjunctiva between the sclera of the eyeball and the lid with the portal oriented towards the globe, and when in place, they will release a therapeutically effective amount of pilocarpine for the internal management of glaucoma to an adult human over a period of 24 hours.

EXAMPLE 11

Ocular dispensing system of elliptical shape for administering a drug to the tissue compartments of the eye over a prolonged period of time and having a length of 4 to 20 millimeters, a width of 1 to 15 millimeters and a thickness of 0.1 to 4 millimeters are prepared by mixing liquid polydimethylsiloxane, chloramphenicol and stannous octate and curing the mixture at room temperature. The resulting matrix is placed in a pre-shaped and sized ethylene-vinyl acetate copolymer tube and the opened end adhesively sealed to provide a solid matrix containing drug. Then, 90% of the exposed surface of the copolymer is surrounded with cross-linked drug impermeable polyamide. The system when placed in the eye with the drug portal oriented towards the palpebral conjunctiva of the eyelid produces no discomfort or irritation and releases drug in a therapeutically effective amount to produce the desired bactericidal effect.

EXAMPLE 12

Milled crystals of hydrocortisone are mixed with ethylene-vinyl acetate copolymer having an acetate content of 22% by weight of the mixture ballmilled for 20 minutes to provide a uniform distribution of drug throughout the polymeric carrier. The resulting mixture is shaped, sized and adapted as a rectangular system. Finally, three sides of the system are laminated with cross-linked drug impermeable polyamide to yield the ocular system having a single drug emitting portal.

EXAMPLES 13 to 15

An ocular therapeutic system, similar to FIG. 1, not shown, in another embodiment is manufactured by distributing ophthalmic drug throughout a 7.5 mm×14 mm×2 mm template of drug release rate controlling ophthalmically acceptable polymeric material formed with a continuous single, drug emitting portal that is permeable to the passage of drug and also functions as a controller which controller releases it at a controlled rate from the system. The side of the system distant therefrom is suitably laminated with a lamina of a material that is completely nonemitting. The drug is mixed with an osmotically effective solute, lithium chloride, which in the environment of use imbibs drug into the system for osmotically releasing it through the single portal. In another embodiment, the system is formed of an erodible polymer having drug dispersed therein and a layer of a drug impermeable material suitably joined thereto. The system releases drug by bioerosion of the single exposed surface of the system. Suitable bioerodible polymers are disclosed in United States Pat. No. 4,001,388 which is incorporated herein by reference. This patent is assigned to the ALZA Corporation of Palo Alto, Calif.

EXAMPLE 16

A drug delivery system for the prolonged release of pilocarpine nitrate to the internal part of the eye is prepared and tested in the following manner: first, a reservoir formed of a drug and a polymer in intimate mixture is prepared according to the described procedure. A 7 gram portion of micronized pilocarpine nitrate is admixed with 3 grams of an ethylene-vinyl acetate copolymer having a vinyl acetate content of about 40% and having a melt index of 45-70 g/min, as measured by ASTM D 1238-modified test. The copolymer has a tensile strength of about 600-700 psi and an elongation at break of 1400% to 1500%. It is impermeable to pilocarpine nitrate but permeable to water. Pilocarpine nitrate is a water soluble drug having a solubility of about 25% in water, and it functions as an osmotically effective solute in the therapeutic system. The pilocarpine nitrate micronized particles are on average ~40 microns in diameter. The mixture is heated to 120° C. and cast as a 0.6 mm thick film. Next, a thin, water and drug impermeable thin film of butyl rubber is laminated to one side of the film thereby forming a system with a single drug portal. Finally, a number of 6 mm discs, suitable in size for insertion and retention in the eye, are cut from the 0.6 mm thick film. These discs have a portal with a surface area of 66 mm$^2$. Osmotic bursting devices are the invention of Michaels and Gulloid as described in United States Patent Application Ser. No. 578,979 filed on May 19, 1975.

The release of drug from the ocular therapeutic system is determined by placing the systems in a simulated ocular aqueous environment. The outermost drug depots imbibs water through the sole exposed surface, swell, and burst their enclosing membranes, releasing their drug from the reservoir and exposing innermost depots. The amount of drug released in this rate controlled osmotic system is monitored by a UV spectrometer set at 215 nanometer wavelength. A relatively rapid release of pilocarpine nitrate begins to be noticed. The release continues for about 22 hours at a rate gradually decreasing from an initial 400 micrograms per hour to about 250 micrograms per hour after 22 hours. After 22 hours, the release rate falls rapidly. Microscopic and macroscopic comparison of the systems before and after use show that they retain their unit configuration but release drug by bursting the polymeric reservoir surrounding the drug depots.

EXAMPLE 17

A bioerodible ocular system 10 made for use according to the invention consists of a bioerodible polymer of a continuous matrix having pilocarpine nitrate dispersed therethrough. The drug containing polymeric system was prepared by dissolving drug and polymer in 1,4-dioxane and the mixture lypophilized then the drug mixture was pressed at 100° C. and 15,000 psi to give a drug-polymer reservoir. Next, a drug impervious layer of butyl rubber was suitably joined to reservoir, except for a single surface defining a portal. Ocular therapeutic systems prepared by this procedure include 10% pilocarpine nitrate and poly(2,2-dioxy-trans-1,4-cyclohexane dimethylene tetrahydrofuran). These systems continuously bioerode and dispense a metered amount of drug to a selected part of the eye. The polymer of this example is the invention disclosed and claimed by Choi and Heller in United States Patent Application Ser. No. 544,808 filed on Jan. 28, 1975, which application is assigned to the ALZA Corporation.

DESCRIPTION OF THE APPLICATION OF THE INVENTION

An in vivo procedure that effectively demonstrates the method of unidirectional release using ocular systems which method gives both improved results and functions at a higher order of therapeutic operability was performed as follows: first a series of ocular systems that release pilocarpine from two sides of the system at rates of 20 micrograms, 40 micrograms and 80 micrograms per hour were placed in the cul-de-sac of New Zealand white rabbits' eyes. After the ocular systems were in the cul-de-sac 24 hours, they were removed, and a tear sample collected for measuring its pilocarpine content. Then, the systems were returned to the cul-de-sac for one-half hour, the rabbits sacrificed, and an aqueous humor sample immediately withdrawn for measuring the pilocarpine content thereof.

The ocular systems that release 80 micrograms per hour have a retention rate in rabbits' eyes approaching zero, and these ocular systems were retained in rabbits' eyes by one of three methods: (1) the ocular systems were placed in the cul-de-sac and the lids were sutured together to close the eye; (2) two conjunctival flaps were made in the area of the cul-de-sac and the ocular systems were placed under the flaps which held the unit in the cul-de-sac; or (3) ocular systems were tethered in the cul-de-sac by running sutures at either end of the long axis of the ocular systems and then into the conjunctiva. The sutures thus placed, restricted the movement of the ocular systems so that lateral and vertical movement of the ocular systems could not exceed a distance of more than 2 mm. Tear samples were collected and processed in the same way as were tear samples from ocular systems releasing 20 and 40 micrograms per hour.

A second set of ocular systems were used in these experiments and they were manufactured with a size and shape that corresponded to the above ocular systems, except that these latter systems were unireleasing ocular systems. That is, the ocular systems released pilocarpine from a single portal. These systems delivered one-half of the amount of the above systems, and they released pilocarpine at the rate of 10 micrograms, 20 micrograms and 40 micrograms per hour. These systems were positioned in the cul-de-sac, with the portal oriented towards the sclera, and tears and aqueous humor samples were taken and analyzed for their pilocarpine content as described above.

The pilocarpine concentration in tears and aqueous humor of rabbits' eyes 24 hours after insertion placement of the ocular therapeutic systems in the cul-de-sac is set forth in Table 1. In Table 1, the ocular systems released pilocarpine from two sides, "S.E.M." is the standard error of the means, "N" is the number of rabbits, "Efficiency" represents the aqueous humor pilocarpine concentration divided by the area of drug releasing surface of the ocular system, "20", "40" and "80" means the ocular systems released 20, 40 and 80 micrograms of pilocarpine per hour, respectively, and "Ocular System Placement" indicates the location and degree of freedom for the ocular systems in the cul-de-sac.

TABLE I

Pilocarpine Concentration In Tears And Aqueous Humor Of Rabbit Eyes 24 Hours After Placement Of Ocular Therapeuic Systems In The Cul-De-Sac

| Ocular System | Ocular System Placement | Area of Drug Releasing Surfaces of Ocular System ($cm^2$) | Mean Pilocarpine Concentration ± S.E.M. Tears (ng/$\mu$l) | Aqueous Humor (ng/$\mu$l) | N | Efficiency |
|---|---|---|---|---|---|---|
| 20 | unrestrained in tears of cul-de-sac | 0.8 | 21.0 ±4.7 | 0.59 ±0.19 | 11 | 0.74 |
| 40 | unrestrained in tears of cul-de-sac | 0.8 | 90.8 ±19.6 | 0.54 ±0.13 | 9 | 0.68 |
| 80 | eyelids sutured together, or systems held in conjunctival flaps | 1.1 | 123.0 ±20.0 | 0.89 ±0.18 | 10 | 0.81 |

The results of the experiments for ocular systems releasing from a single drug emitting portal are set forth in Table II. In Table II, the two ocular systems identified as (a) and (b) release pilocarpine from two surfaces at a total rate of 20 and 40 micrograms per hour. The ocular systems identified as (c) release pilocarpine from a single drug emitting membrane at a rate of 20 micrograms per hour. This latter ocular system in one group of rabbits had the drug emitting portal oriented towards the bulbar conjunctiva, and in another group of rabbits the drug emitting portal was oriented towards the palpebral conjunctiva. The terms in Table II that are common to Table I are defined above. The results of the experiments as seen in Tables I and II clearly indicate that orientation of the drug emitting portal towards the drug receiving membrane leads to unexpected and enhanced results as the experiments show pilocarpine is absorbed from the tear film on the bulbar side of the ocular system and it is transferred into the aqueous humor at least 10 times greater than the absorption and transfer of pilocarpine into the aqueous humor from the palpebral side of the ocular system.

TABLE II

Pilocarpine Concentration In Tears And Aqueous Humor Of Rabbit Eyes 24 Hours After Placement Of Ocular Therapeuic Systems In The Cul-De-Sac

| Ocular System | Ocular System Placement | Area of Drug Releasing Surfaces of Ocular System ($cm^2$) | Mean Pilocarpine Concentration ± S.E.M. Tears (ng/$\mu$l) | Aqueous Humor (ng/$\mu$l) | N | Efficiency |
|---|---|---|---|---|---|---|
| 20 (a) | unrestrained in tears of cul-de-sac | 0.8 | 21.0 ±4.7 | 0.59 ±0.19 | 11 | 0.74 |
| 40 (b) | unrestrained in tears of cul-de-sac | 0.8 | 90.8 ±19.6 | 0.54 ±0.13 | 9 | 0.68 |
| 20 (c) | unrestrained in tears of cul-de-sac (1) bulbar oriented | 0.4 | 32.9 ±5.5 | 0.62 ±.29 | 8 | 1.55 |
|  | (2) palpebral oriented | 0.4 | 34.5 | 0.067 | 8 | 0.17 |

TABLE II-continued

Pilocarpine Concentration In Tears And Aqueous Humor Of Rabbit Eyes
24 Hours After Placement Of Ocular Therapeuic Systems In The Cul-De-Sac

| Ocular System | Ocular System Placement | Area of Drug Releasing Surfaces of Ocular System (cm$^2$) | Mean Pilocarpine Concentration ± S.E.M. | | N | Efficiency |
|---|---|---|---|---|---|---|
| | | | Tears (ng/μl) | Aqueous Humor (ng/μl) | | |
| | | | ±7.7 | ±0.022 | | |

Further evidence indicating a more efficient transfer of drug into an eye drug receptor when a drug emitting portal is oriented towards the receptor is seen in Table III. The results in Table III show a more efficient transfer of pilocarpine into aqueous humor from the bulbar side of an ocular system than from the palpebral side. In Table III, the ocular systems identified as (d) and (e) are systems manufactured with two drug releasing portals with the systems having a total release of 40 to 80 micrograms per hour. The ocular system identified by (f) has a single drug emitting portal and it releases 40 micrograms per hour. The results of Table III further indicate that when the system having a single drug emitting portal that releases 40 micrograms per hour is oriented towards the bulbar conjunctiva, the aqueous humor levels are comparable to those obtained for systems releasing pilocarpine from two portals at a total rate of 80 micrograms per hour. This result is like that found with systems having two drug releasing surfaces releasing a total of 40 micrograms per hour and systems having a single drug emitting portal releasing 20 micrograms per hour as reported in Table II. The mean aqueous humor pilocarpine concentration in rabbits' eyes with bulbar conjunctival oriented single drug emitting portal systems releasing 40 micrograms per hour is at least 10 times that in rabbits' eyes with palpebral conjunctiva oriented single drug emitting portal systems releasing 40 micrograms of pilocarpine per hour. This result parallels the results obtained with single drug emitting portal systems releasing 20 micrograms of pilocarpine per hour. Also, like the results obtained with the latter systems, the tear film concentrations produced by single drug emitting portal systems are approximately one-half that produced by the correspondingly shaped system releasing pilocarpine from two surfaces at a combined rate of 80 micrograms per hour.

TABLE III

Pilocarpine Concentration In Tears And Aqueous Humor Of Rabbit Eyes
24 Hours After Placement Of Ocular Therapeuic Systems In The Cul-De-Sac

| Ocular System | Ocular System Placement | Area of Drug Releasing Surfaces Of Ocular System (cm$^2$) | Mean Pilocarpine Concentration ± S.E.M. | | N | Efficiency |
|---|---|---|---|---|---|---|
| | | | Tears (ng/μl) | Aqueous Humor (ng/μl) | | |
| 40 (d) | unrestrained in tears of cul-de-sac | 0.8 | 90.8 ±19.6 | 0.54 ±0.13 | 9 | 0.68 |
| 80 (e) | both ends of system attached to conjunctiva with sutures | 1.1 | 43.0 ±6.0 | 1.67 ±0.29 | 4 | 1.52 |
| 40 (f) | unrestrained in tears of cul-de-sac | | | | | |
| | (1) bulbar oriented | 0.55 | 16.7 ±3.6 | 2.40 ±0.53 | 8 | 4.36 |
| | (2) palpebral oriented | 0.55 | 23.5 ±3.2 | 0.27 ±0.031 | 7 | 0.49 |

Statistical analysis of data obtained from the above-described experiments was conducted using the Wilcoxon-Mann-Whitnes non-parametric statistic procedures reported in Arch. Ophthalmol., Vol. 94, pages 644 to 652, 1976. The results of the statistical analysis are reported in Table IV. In Table IV, "Free" means the ocular system is unrestricted in the cul-de-sac, "Tethered" means the system is fixed as described above, "Bulbar" means the drug emitting portal was faced towards the bulbar conjunctiva, "Palpebral" means the drug emitting portal was faced towards the palpebral conjunctiva, the numbers "20", "40", and "80" indicate the amount of pilocarpine released in micrograms per hour from the system, "Single-membrane" means the ocular system released its drug from a single drug emitting membrane, or portal, and for the other system, the drug was released from two surfaces, or portals.

TABLE IV

STATISTICAL ANALYSIS OF DATA

| Tears | Confidence Level from Two-Sided Probability Table |
|---|---|
| 20 < 40"$_{free}$" | p < 0.02 |
| 40 = 80"$_{free}$" | p > 0.05 |
| 80"$_{free}$" > 80"$_{tethered}$" | p < 0.02 |
| 20 = single membrane 20$_{bulbar}$ | p > 0.05 |
| 20 = single membrane 20$_{palpebral}$ | p > 0.05 |
| 20 = single membrane 40"$_{tethered}$" bulbar | p > 0.05 |
| 20 = single membrane 40"$_{tethered}$" palpebral | p > 0.05 |
| Aqueous Humor | |
| 20 = 40 = 80"$_{free}$" | p > 0.05 |
| 80"$_{free}$" < 80"$_{tethered}$" | p < 0.05 |
| 20 = single membrane 20$_{bulbar}$ | p > 0.05 |
| 20 > single membrane 20$_{palpebral}$ | p < 0.02 |

TABLE IV-continued

STATISTICAL ANALYSIS OF DATA

| Tears | Confidence Level from Two-Sided Probability Table |
|---|---|
| 80"$_{tethered}$" = single membrane 40"$_{tethered}$" bulbar | $p > 0.05$ |

A multiplicity of studies were performed for measuring the drug concentration in tissue compartments of the eye of drug delivered from a series of ocular systems having a single drug emitting portal, and ocular systems having two drug emitting portals. The results of the studies indicated the concentration of drug in the tissue is ascertainable from measurable system parameters, namely the rate of release of drug and the surface area of the portal. The studies demonstrated the unexpected correlation between the surface area of the portal, the rate of release and the concentration of drug in the tissue.

The studies were carried out as follows: first, ocular systems manufactured according to examples 1 through 17 were washed in water at 37° C. for 24 hours so that drug was released at zero order rates at the time the system was placed in the animal eye cul-de-sac. The systems were placed in the lower cul-de-sac of either the left or the right eye, and remained there for a known time period, for example, 2 hours, at which time the aqueous humor drug concentration, in this study the drug is pilocarpine, was in a steady state.

The aqueous humor was sampled within 30 seconds of the system removal from the eye. The eye was proptosed, and the sample withdrawn from the anterior chamber with a #30 needle and a 1 cc tuberculin syringe. The aqueous sample was placed into a pre-weighed labelled vial. The vial was reweighed, and the net weight of aqueous humor collected was recorded. Each collected aqueous humor sample was stored in 1 ml nanograde methyl alcohol at 4° C., for future pilocarpine assay.

The pilocarpine was determined and the standards used in the assay were 500 pg, 1.0, 2.0, and 4.0 ng pilocarpine. Methazolamide was used as an internal standard. The heptafluorobutyric derivatives of pilocarpine were detected by election capture gas chromatography using a Varian Aerograph ® Model 2100, with a 3% OV17 on Chromosorb Column at 195° C.

The study demonstrated the effect of the rate of release on aqueous humor pilocarpine concentration; while, holding the surface area constant of the drug emitting portal and varying the rate of release per system side at 5, 10, and 20 µg/hr. The study also demonstrated the effect of surface area on aqueous humor pilocarpine concentration, while holding the release rate constant, and varying the surface area of one portal from 0.4 to b 0.67 cm$^2$.

Figure 6:
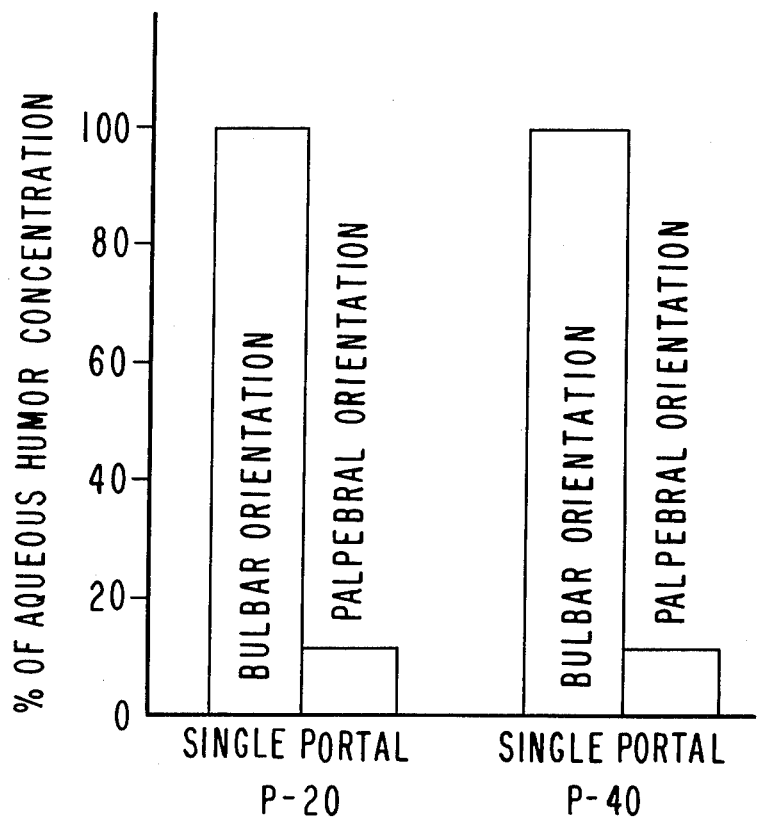
FIG. 6 is a bar graph illustrating the steady state aqueous humor pilocarpine concentration during drug delivery from single portal systems.
Figure 7:
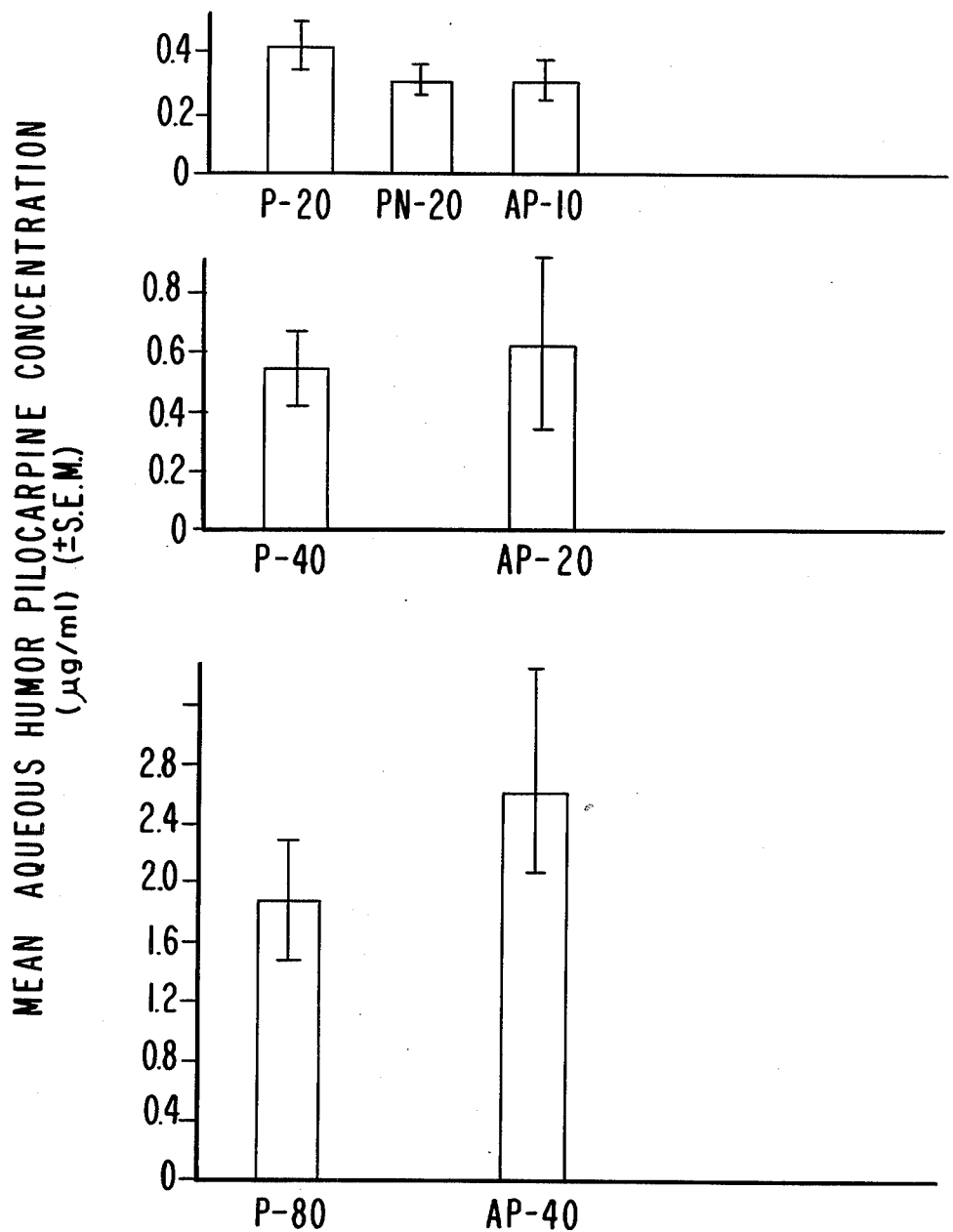
FIG. 7 is a graph illustrating steady state aqueous humor pilocarpine concentration during drug delivery only toward the bulbar conjunctiva or toward both palpebral and bulbar conjunctiva.

The unexpected results and benefits of the invention are further illustrated in FIGS. 6 through 10, and in Tables 5 and 6. The results for a drug delivery system having a single drug releasing portal, with the portal oriented towards the bulbar conjunctiva, or with the portal oriented towards the palpebral conjunctiva are set forth in FIG. 6. In FIG. 6, the notations P-20 and P-40 indicate a rate of release of pilocarpine from a single portal of 20 µg/hr and 40 µg/hr of pilocarpine respectively. The mean aqueous humor pilocarpine concentration produced by delivering drug only towards the palpebral conjunctiva was 11% of the mean concentration produced by delivering drug only towards the bulbar conjunctiva. Therefore, for a given drug delivery rate, a single portal emitting system oriented towards the bulbar conjunctiva should produce a mean aqueous drug concentration close to that produced by a system delivering pilocarpine at a given rate from two sides of the system, that is, towards the palpebral conjunctiva as well as towards the bulbar conjunctiva. The steady state aqueous humor concentration during drug delivered only towards the bulbar conjunctiva or towards both palpebral and bulbar conjunctiva is set forth in FIG. 7. In FIG. 7 there are three data sets in which a single drug emitting portal system is matched by surface area per side and the rate of release per portal with systems made with two drug emitting portals. In FIG. 7, S.E.M. denotes standard error of the means, P-20 denotes a system having two portals releasing drug by diffusion at a rate of release of 10 µg/hr per portal for a total release of 20 µg/hr; PN-20 denotes a system having two portals releasing drug by osmotic bursting at a rate of 10 µg/hr per portal for a total release of 20 µg/hr; AP-10 denotes a system having a single drug emitting portal releasing drug by diffusion at the rate of release of 10 µg/hr; P-40 denotes a system having two drug emitting portals each releasing 20 µg/hr by diffusion for a total of 40 µg/hr; AP-20 denotes a system having a single drug emitting portal releasing 20 µg/hr by diffusion; P-80 denotes a system having two drug emitting portals each releasing 40 µg/hr by diffusion for a total of 80 µg/hr; and, AP-40 denotes a system having a single drug emitting portal releasing 40 µg/hr by diffusion, the osmotic system housing pilocarpine nitrate produces aqueous concentrations which are substantially similar to those produced by diffusional systems.

Figure 8:
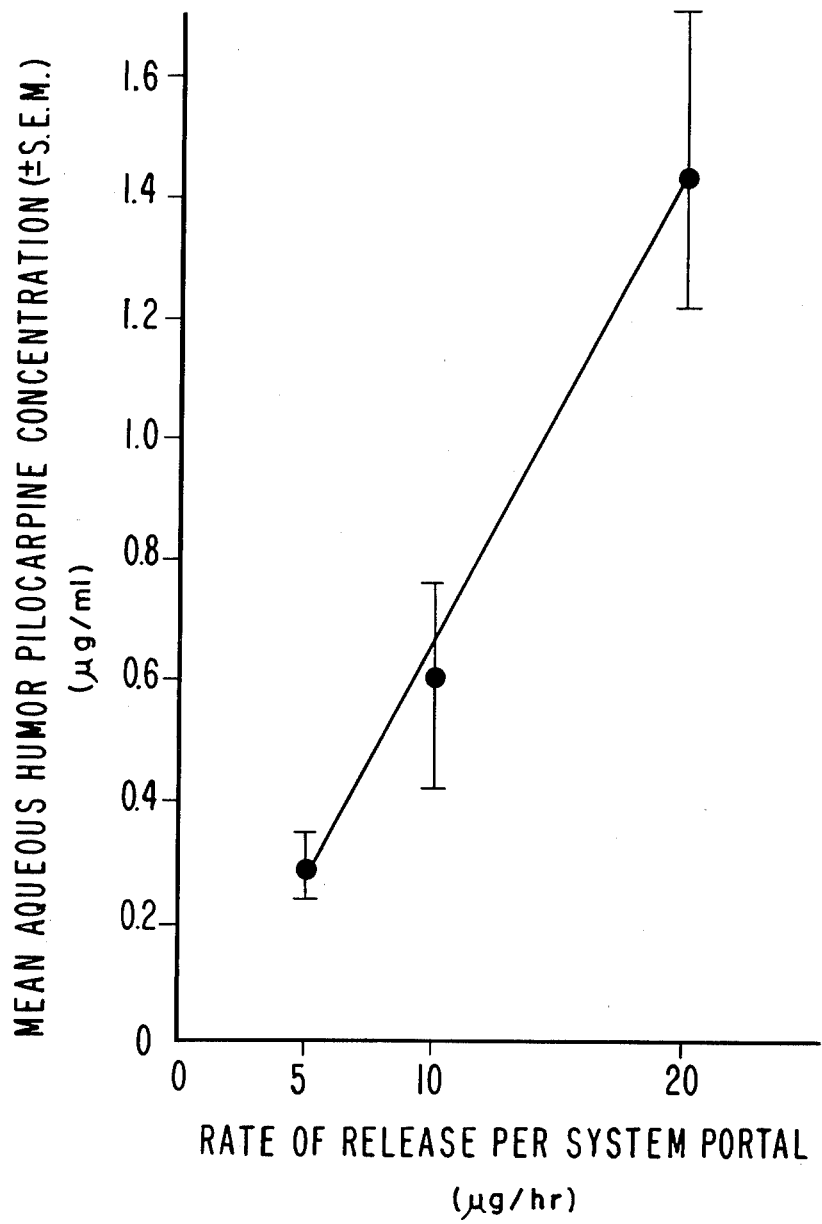
FIG. 8 is a graph illustrating the effect of the rate of release on steady state aqueous humor pilocarpine concentration at a constant surface area.

The effect of the rate of release on steady state aqueous humor concentration at a constant surface area, equal to 0.67 cm$^2$, is depicted in FIG. 8. The systems employed in this study released drug by osmotic bursting with an aqueous humor pilocarpine concentration increase of 0.4 µg/ml per 5 µg/hr increase in the rate of release per portal. The aqueous humor pilocarpine concentration is directly proportional to the rate of release from 5 to 20 µg/hr per portal at a constant surface area per portal, of 0.67 cm$^2$. By linear regression analysis, the coefficient of correlation is 0.996.

Figure 9:
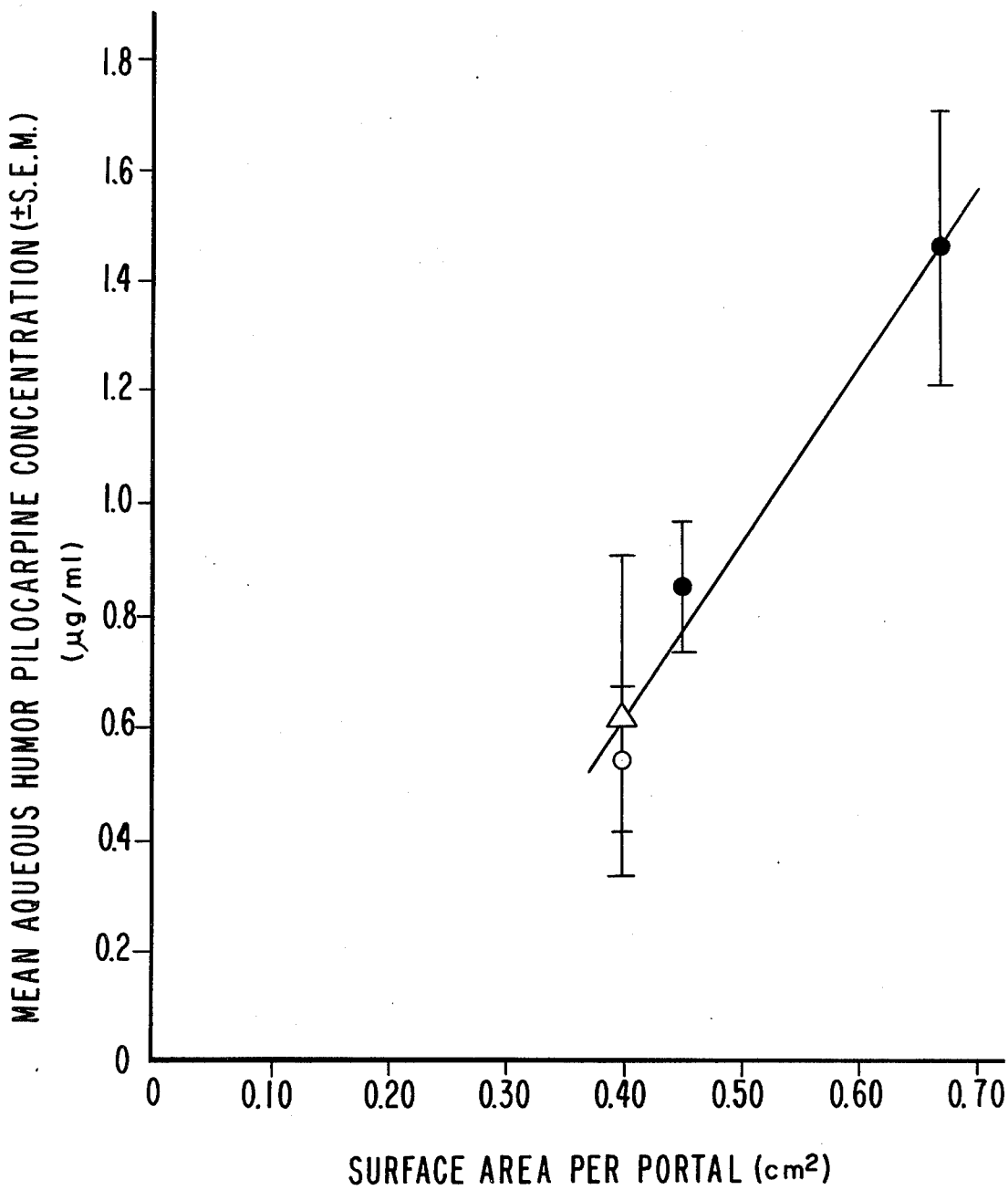
FIG. 9 illustrates the effect of surface area per system portal on steady state aqueous humor pilocarpine concentration at a constant rate of release per system portal.

The effect of surface area per portal on steady state aqueous humor pilocarpine concentration at a constant rate of release is illustrated in FIG. 9. In FIG. 9, the clear circles represent systems releasing drug by diffusion, the darker circles represent systems releasing drug by osmotic bursting, and the triangle represents systems having a single drug emitting portal. The results show the aqueous humor pilocarpine concentration is proportional to the surface area of the portal from 0.40 to 0.67 cm$^2$ per system portal at a constant rate of release of 20 µg/hr. The aqueous humor pilocarpine concentration increases 0.32 µg/ml per 0.1 cm$^2$ increase in surface area per side. By linear regression analysis, the coefficient by correlation is 0.989, indicating correlation between aqueous humor drug concentration and surface area per portal of the system.

Figure 10:
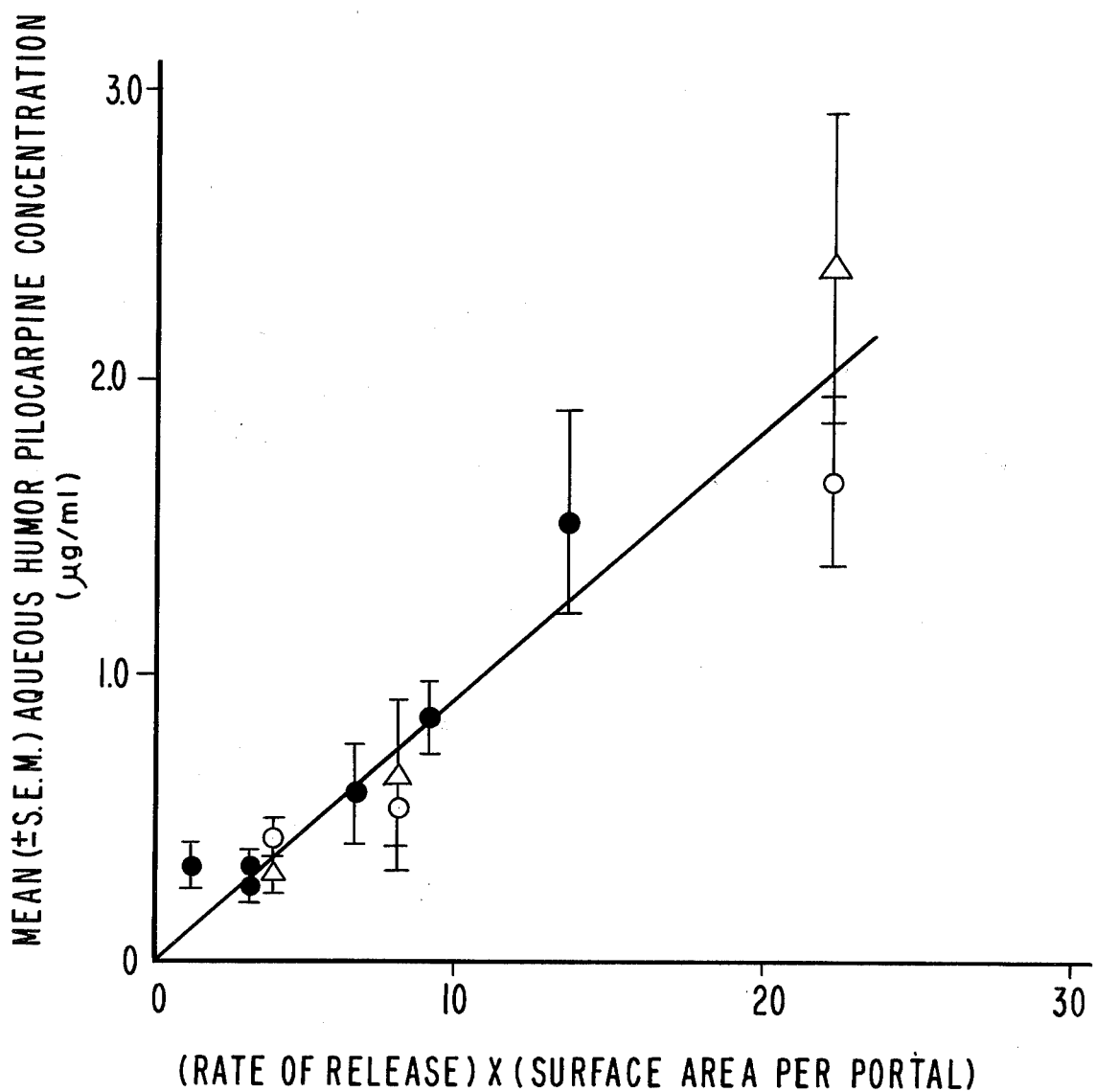
FIG. 10 illustrates the effect of release and surface area on steady state aqueous humor pilocarpine concentration.

The effects of the rate of release and surface area on steady state aqueous humor pilocarpine concentration is illustrated in FIG. 10. In the Figure, the clear circles indicate diffusional systems, the darkened circles osmotic systems and the triangle asymmetrical diffusional systems having a single drug emitting portal. The study pertained to the correlation between aqueous humor pilocarpine concentration, the dependent variable, and the surface area per portal and the rate of release per portal by three variable linear regression analysis. The correlation coefficient of the regression is 0.925, demonstrating correlation between the three variables. FIG. 10 shows a two-dimensional plot for the product of the rate of release per portal and the surface area per portal given as the independent variable. In operation, to use the product of rate of release per drug emitting portal and surface area per portal to indicate the tissue compartment drug concentration, the studies show a high correlation between the product of the two independent variables and the tissue compartment drug concentration, which by linear regression analysis evidences a correlation coefficient of 0.958.

The effect of surface area and the rate of release on rabbit eye aqueous humor pilocarpine concentration is listed in Table V. In the table, System indicates an ocular therapeutic system; PN-10 indicates a system releasing drug from two portals by osmotic release for a total rate of release 10 μg/hr; PN-20 indicates a system releasing drug from two portals by osmotic release for a total rate of release of 20 μg/hr; AP-10 (bulbar) indicates a system releasing drug from a single portal by diffusion with the portal oriented towards the bulbar conjunctiva with a rate of release of 10 μg/hr; P-20 indicates a system releasing drug by diffusion from two portals at a total rate of release of 20 μg/hr; PN-20 indicates a system releasing drug by osmotic releasing from two portals at a total rate of release of 20 μg/hr; AP-20 (bulbar) indicates a system releasing drug by diffusion from a single drug emitting portal oriented towards the bulbar conjunctiva at a rate of release of 20 μg/hr for the single emitting portal; P-40 indicates a system having two drug emitting portals releasing a total of 40 μg/hr by diffusion; PN-40 indicates a system having two drug emitting portals releasing a total of 40 μg/hr by osmotic releasing; AP-40 (bulbar) indicates a system having a single drug emitting system releasing 40 μg/hr by diffusion for the single portal; P-80 indicates a system having two drug emitting portals releasing drug by diffusion at a total rate of release of 80 μg/hr for the two portals; AP-20 (palpebral) indicates a system having a single drug emitting portal oriented in the eye towards the palpebral conjunctiva releasing drug by diffusion at a rate of 20 μg/hr; AP-40 indicates a system having a single drug emitting portal oriented towards the palpebral conjunctiva releasing drug by diffusion at a rate of 40 μg/hr, and the asterisk after humor denotes standard error of means.

The correlation between the concentration of drug in the tear film and the concentration of drug in the aqueous humor is set forth in Table VI. In the table, AP-20 indicates a system having a single drug emitting portal releasing pilocarpine by diffusion at the rate of 20 μg/hr; P-40 indicates a system having two drug emitting portals releasing pilocarpine from both portals by diffusion at a total rate of 40 μg/hr; bulbar indicates the single portal is oriented towards the bulbar conjunctiva, palpebral indicates the single portal is oriented towards the palpebral conjunctiva, and the plus-minus signs before a number indicates the standard error of the mean.

TABLE V
EFFECT OF SURFACE AREA AND RELEASE RATE ON RABBIT EYE AQUEOUS HUMOR PILOCARPINE CONCENTRATION

| Ocular Therapeutic System | Releaase Rate/Side times Surface Area/Side | Aqueous Humor* Pilo. Conc. (μg/ml) | N | Surface Area per side (cm$^2$) | Release Rate per side (μg/hr) |
|---|---|---|---|---|---|
| PN-10 | 3.4 | 0.29 ± 0.06 | 6 | 0.67 | 5 |
| PN-20 | 3.5 | 0.31 ± 0.04 | 8 | 0.35 | 10 |
| AP-10 (bulbar) | 4.0 | 0.31 ± 0.07 | 8 | 0.40 | 10 |
| P-20 | 4.0 | 0.41 ± 0.08 | 18 | 0.40 | 10 |
| PN-20 | 6.7 | 0.59 ± 0.17 | 8 | 0.67 | 10 |
| AP-20 (bulbar) | 8.0 | 0.62 ± 0.29 | 8 | 0.40 | 20 |
| P-40 | 8.0 | 0.54 ± 0.13 | 9 | 0.40 | 20 |
| PN-40 | 9.0 | 0.85 ± 0.12 | 7 | 0.45 | 20 |
| PN-40 | 13.4 | 1.46 ± 0.25 | 8 | 0.67 | 20 |
| AP-40 (bulbar) | 22.0 | 2.40 ± 0.53 | 8 | 0.55 | 40 |
| P-80 | 22.0 | 1.67 ± 0.29 | 4 | 0.55 | 40 |
| AP-20 (palpebral) | 8.0 | 0.06 ± 0.02 | 7 | 0.40 | 20 |
| AP-40 (palpebral) | 22.0 | 0.27 ± 0.03 | 7 | 0.55 | 40 |

TABLE VI
Relationship Between Tear Film And Aqueous Humor

| Ocular Therapeutic System | Tear Film | Aqueous Humor | Area per System Portal |
|---|---|---|---|
| Ap-20 bulbar | 32.9 ±5.5 | 0.62 ±0.29 | 0.40 cm$^2$ |
| palpebral | 34.6 ±7.7 | 0.068 ±0.022 | 0.40 cm$^2$ |
| P-40 | 82.0 ±18.1 | 1.46 ±0.25 | 0.67 cm$^2$ |
| P-40 | 90.8 ±19.6 | 0.54 0.13 | 0.40 cm$^2$ |

Selection of an ocular drug receptor site for administering a drug thereto can be easily ascertained by following the above procedures. Those skilled in the art can readily determine the biological site with the ocular systems of this invention by orienting the drug emitting portal towards the selected part or parts of the eye and then measure the physiological effect or the absorption and uptake of drug. For example, the physiological effect can be determined by measuring ocular pressure and increased vision. The concentration of drug in a biological specimen can be measured by various physical and chemical techniques including desorption or extraction of the drug from the specimen with a suitable solvent for the drug, change in weight, histological examination, pyrolysis, and immuno assay. Treated and untreated specimens can be analyzed by standard techniques including ultraviolet, radio isotope, visible spectrophotometry, flame photometry, refractive index, gas chromatography, thin layer chromatography, polarimetry, chemical analysis and density measurements. Procedures for determining the amount of drug in biological specimens are known to the art as recorded in Arch.

Ophthal., Vol. 74, pages 248 to 252, 1963; in ibid., Vol. 75, pages 689 to 692, 1966; J. Pharm. Sci., Vol 59, pages 1559 to 1563, 1970; in J. Am. Med. Assoc., Vol. 194, No. 11, pages 1203 to 1205, 1965; in J. Pharm. Sci., Vol. 57, pages 378 to 384, 1968; and in Amer. J. of Ophthal., Vol. 80, No. 2, pages 274 to 283, 1975. In the present studies, the concentration of pilocarpine was determined by acylating the imidazole ring of pilocarpine with heptaflurobutyric anhydride using triethylamine as a catalyst. The pilocarpine derivative was analyzed using gas chromatography with electon-capture detection. The assay has a sensitivity of 25–50 picograms of pilocarpine and it is specific for pilocarpine. The isopilocarpine derivative is eluted prior to the pilocarpine derivative. The procedures used in this assay are reported in J. Pharm. Sci., Vol. 51, page 1095, 1962; in J. Chrom., Vol. 19, pages 296, 1965; in Anal. Chem., Vol. 37, page 952, 1965; in J. Pharm Sci., Vol. 60, page 1468, 1971; in J. Chem., Vol. 51, page 2315, 1973; in J. Am. Chem. Soc., Vol. 95, page 2297, 1973; and in J. Chem. Soc., page 3019, 1959; and the references cited therein.

Additional examples of specific directional release of drug from an ocular system having a single portal used for administering drug internally for the management of an internal condition is effected by orienting the portal towards the bulbar conjunctiva. Medical conditions treated by this method of orientation include glaucoma, thrombosis, iritis, iridocyclitis, and uveitis. Further orientation of the portal includes towards the bulbar conjunctiva, that, the sclera for treating scleritis; orienting the portal towards the interior surface or the palpebral conjunctiva of the eyelid for releasing hydrocortisone, bacitracin, neomycin, fluocinolone acetamide, bethamethasone 17-valerate, sulfonamide and idoxuridine for the management of bacterial infections, herpes zoster, herpes simplex and fungus infections; orienting the portal towards the palpebral conjunctiva for treating chemical burns with broad spectrum antibiotics; orienting the portal towards the cornea for treating inflammation of the cornea with steroids; having the portal faced towards the palpebral conjunctiva for drug entry into the tear film and thence into the nasopharyngeal duct; and facing the portal toward vascularized conjunctiva for introducing drug into systemic circulation.

The ocular therapeutic systems and the method of the invention can be used by the medical and the veterinary ophthalmic arts for the management of ocular health and disease. And, while the above examples, figures and disclosures are set forth for illustrating the mode and the manner of the invention, various modifications and embodiments can be made by those skilled in the ophthalmic art in the light of the invention without departing from the spirit of the invention.

I claim:

1. A method for administering drug to a preselected surface of the lid of an eye comprising the steps of:
   (a) placing in the eye a therapeutic system comprising: a drug, a drug delivery module sized, shaped and adapted as a platform for comfortable retention in the eye and for housing the drug, said module including a delivery portal defining a surface area of the module for releasing the drug from the system; and,
   (b) positioning the system in the eye by orienting the portal towards the preselected internal surface of the lid for effective administration of drug thereto.

2. The method for administering drug according to claim 1, wherein the drug is released by diffusion, osmosis, or bioerosion from the system.

3. A method for administering drug internally into the eye comprising the steps of:
   (a) placing in the eye a therapeutic system comprising: a drug, a drug delivery module sized, shaped and adapted as a platform for comfortable retention in the eye and for housing the drug, said module including a delivery portal defining a surface area of the module for releasing the drug from the system; and,
   (b) positioning the system in the eye by orienting the portal towards the globe of the eye for administering drug internally for effective administration of drug thereto.

4. A method for administering drug to a preselected surface of the lid of an eye comprising the steps of:
   (a) placing in the eye a therapeutic system comprising: a drug delivery module sized, shaped and adapted as a platform for comfortable retention in the eye, said module including (1) a reservoir, (2) a drug housed in the reservoir, and (3) a portal defining a single surface of the module for releasing drug from the system; and,
   (b) positioning the system in the eye by orienting the portal towards the preselected internal surface of the lid for effective administration of drug thereto.

5. The method for administering drug according to claim 4, wherein the preselected surface of the lid is the palpebral conjunctiva and the portal is in intimate contact with a preselected area thereof for selectively administering drug thereto.

6. The method for administering drug according to claim 4, wherein the portal releases drug into the tear film of the eye positioned between the portal and the internal surface of the lid, which film functions as a drug reservoir for transferring drug to the preselected internal surface of the lid.

7. The method for administering drug according to claim 4, wherein the portal is a rate controller for governing the rate of release of drug in a therapeutically effective amount from the system.

8. A method for administering a drug internally into the eye comprising the steps of:
   (a) placing in the eye a therapeutic system comprising a drug delivery module sized, shaped and adapted as a platform for comfortable retention in the eye, said module including: (1) a reservoir; (2) a drug housed in the reservoir; (3) a portal defining a single surface area of the module, said portal a means for releasing drug from the system;
   (b) positioning the system in the eye by orienting the portal towards the globe of the eye for administering drug internally for effective administration of drug to produce a desired beneficial effect.

9. The method for administering drug internally to the eye according to claim 8, wherein the portal of the system is oriented towards the sclera of the globe of the eye for releasing drug thereto.

10. The method for administering drug internally to the eye according to claim 9, wherein the portal of the system is oriented towards the cornea of the globe of the eye for releasing drug thereto.

11. The method for administering drug internally to the eye according to claim 9, wherein the portal of the system is oriented towards the bulbar conjunctiva, and the system releases drug by means selected from the group consisting of diffusion, osmosis and bioerosion.

12. The method for administering drug internally to the eye according to claim 9, wherein the module is formed of a polymeric material which material is the reservoir housing drug, and the portal is a single drug emitting surface with the remaining surfaces of the system substantially impermeable to the passage of drug.

13. A method for admitting drug into the nasal pharyngeal duct which method consists essentially of:
 (a) placing in the eye a therapeutic system comprising a drug delivery module, sized, shaped and adapted for comfortable retention in the eye, said module comprising: (1) a reservoir; (2) a drug housed in the reservoir; (3) a portal defining a single surface area of the module, said portal a means for releasing drug from the reservoir; and,
 (b) positioning the system in the eye and orienting the drug delivery portal towards the palpebral conjunctiva for releasing drug into the tear film of the eye for passage through the punctum into the nasal pharyngeal duct.

14. The method for administering drug according to claim 13, wherein the module is formed of a polymeric material, which material is the reservoir housing drug, and the drug emitting portal is a surface of the module.

15. In a method for administering drug into systemic circulation comprising the steps of:
 (a) inserting in the eye of a warm blooded animal a therapeutic system comprising a drug delivery module sized, shaped and adapted for prolonged retention in the eye, said module formed of a pharmaceutically acceptable polymeric material comprising: (1) a reservoir; (2) a drug confined in the reservoir; (3) a portal defining a sole surface area of the material with the remaining surfaces of the system substantially impermeable to the passage of drug, said portal a means for emitting drug from the reservoir; and,
 (b) orienting the portal towards a preselected part of the eye capable of receiving a drug for administering the drug into systemic circulation for producing a beneficial response at a drug receiving tissue site distant from the eye.

16. In a method for administering drug into systemic circulation according to claim 15, wherein the module is a monolithic structure formed of a solid polymeric material with the drug confined therein.

17. In a method for administering drug into systemic circulation according to claim 15, wherein the portal is a rate controller means for controlling the rate of release of drug from the reservoir in a therapeutically effective amount over a prolonged period of time, and the drug is a systemically acting drug.

18. The method for administering a drug internally into the eye according to claim 4 wherein the drug is hydrocortisone, dexamethasone, fluocinolone, medrysone, prednisolone, fluoromethalone, bethethasone or triaminolone.

19. The method for administering a drug internally into the eye according to claim 4 wherein the drug is pilocarpine, physotigmine, eserine, carbachol, insulin, phospholine iodine, demecarium bromide, atropine, cyclopentolate, homatropine, scopolamine, tropicamide, eucatropine, hydroxyamphetamine, ephedrine, or epinephrine.

20. The method for administering a drug internally into the eye according to claim 4 wherein the drug is tetracycline, chlortetracycline, bacitacin, neomycin, polymyxin, gramicidin, cephalexin, oxytetracycline, chloramphenicol, kanamycin, gentamycin, erythromycin, penicillin, sulfamethiazole, sulfisoxazole, nitrofurazon, interferon, or idoxuridine.

21. The method for administering a drug to the surface of the lid of the eye according to claim 6 wherein the drug is hydrocortisone, dexamethasone, fluocinolone, merdysone, prednisolone, fluoromethalone, bethethasone, or triaminolone.

22. The method for administering a drug to the surface of the lid of the eye according to claim 6 wherein the drug is tetracycline, chlortetracycline, bacitracin, neomycin, polymyxin, gramicidin, cephalexin, oxytetracycline, chloramphenicol, kanamycin, gentamycin, erythromycin, penicillin, sulfonamide, sulfadrazine, sulfacetamide, sulfamethiazole, sulfisoxazole, nitrofurazone, interferon, or idoxuridine.

23. The method for administering a drug to the surface of the lid of the eye according to claim 6 wherein the drug is pilocarpine, physotigmine iodine, demecarium bromide, atropine, cyclopentoloate, homatropine, scopolamine, tropicamide, eucatropine, hydroxyamphetamine, ephedrine, or epiniphrine.

24. The method for administering drug according to claim 6 wherein the module is formed of a polymeric material which material is a reservoir for housing the drug and the portal is the single drug emitting surface of the system.

25. The method for administering drug internally into the eye according to claim 14 wherein the drug housed in the reservoir is pilocarpine, physotigmine, eserine, carbachol, insulin, atropine, homatropine, scopolamine, ephedrine, or epinephrine.

26. The method for administering drug internally to the eye according to claim 14 wherein the portal releases drug into the tear film of the eye positioned between the portal and the bulbar conjunction of the globe, which tear film serves as a drug reservoir for transferring drug internally to the eye and the portal functions as a controller means for regulating the rate of release of drug in a therapeutically effective amount from the system.

27. The method for administering drug into systemic circulation according to claim 23, wherein the module is formed of a pharmaceutically acceptable polymeric material and the reservoir is a container therein, with drug administered from the portal of the ocular therapeutic system with minimal lateral dispersion of drug from said system.

* * * * *